US012758534B2

(12) United States Patent
Arkin et al.

(10) Patent No.: US 12,758,534 B2
(45) Date of Patent: Oct. 13, 2026

(54) TREATMENT AND PREVENTION OF BASAL CELL CARCINOMA WITH TOPICAL COMPOSITION COMPRISING PATIDEGIB

(71) Applicant: Sol-Gel Technologies Ltd., Ness Ziona (IL)

(72) Inventors: Moshe Arkin, Kfar Shmaryahu (IL); Ofra Levy-Hacham, Ness Ziona (IL); Ofer Toledano, Kfar Saba (IL); Ervin Epstein, Ness Ziona (IL); Jean Tang, Ness Ziona (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 0 days.

(21) Appl. No.: 19/266,342

(22) Filed: Jul. 11, 2025

(65) Prior Publication Data

US 2025/0339408 A1 Nov. 6, 2025

Related U.S. Application Data

(63) Continuation-in-part of application No. PCT/IL2024/050047, filed on Jan. 11, 2024.

(60) Provisional application No. 63/438,543, filed on Jan. 12, 2023.

(51) Int. Cl.
*A61K 31/4355* (2006.01)
*A61P 35/00* (2006.01)

(52) U.S. Cl.
CPC .......... *A61K 31/4355* (2013.01); *A61P 35/00* (2018.01)

(58) Field of Classification Search
CPC ............................ A61K 31/4355; A61P 35/00
See application file for complete search history.

(56) References Cited

U.S. PATENT DOCUMENTS

| | | | |
|---|---|---|---|
| 8,785,635 | B2 | 7/2014 | Austad et al. |
| 10,695,344 | B2 | 6/2020 | Brown et al. |
| 2009/0181997 | A1 | 7/2009 | Grayzel et al. |

OTHER PUBLICATIONS

Clinical Trial NCT02762084 (PellePharm Inc, study closed Jul. 23, 2020; references from V10 study update Jul. 8, 2020; henceforth NCT '084). (Year: 2020).*

Epstein, Ervin H., et al. "Hedgehog pathway inhibition by topical patidegib to reduce BCC burden in patients with basal cell nevus (Gorlin) syndrome." (2018): e21626 (Year: 2018).*

Clinical Study Protocol from Clinical Trial NCT02762084 (PellePharm Inc, study closed Jul. 23, 2020; henceforth NCT '084). (Year: 2020).*

Cosio, T. et al. (2021). Patidegib in dermatology: a current review. *International Journal of Molecular Sciences*, 22(19), 10725.

Digiovanna, J. J. et al. (2012). Shining a light on xeroderma pigmentosum. *Journal of Investigative Dermatology*, 132(3), 785-796.

Farndon, P. A. et al. (1992). Location of gene for Gorlin syndrome. *The Lancet*, 339(8793), 581-582.

International Search Report and the Written Opinion of the International Searching Authority dated Apr. 9, 2024, issued for the corresponding PCT International Application No. PCT/IL2024/050047, dated Jan. 11, 2024.

International Preliminary Report on Patentability (Chapter I of the PCT) dated Jul. 24, 2025, issued for the corresponding PCT International Application No. PCT/IL2024/050047, dated Jan. 11, 2024.

Khamaysi, Z. et al. (2016). Segmental basal cell naevus syndrome caused by an activating mutation in smoothened. *British Journal of Dermatology*, 175(1), 178-181.

Kiprono, S. K. et al. (2014). Histological review of skin cancers in African Albinos: a 10-year retrospective review. *BMC Cancer*, 14(1), 157.

Macdonald, D. S. (2015). A systematic review of the literature of nevoid basal cell carcinoma syndrome affecting East Asians and North Europeans. *Oral Surgery, Oral Medicine, Oral Pathology and Oral Radiology*, 120(3), 396-407.

Peris, K. et al. (2019). Diagnosis and treatment of basal cell carcinoma: European consensus-based interdisciplinary guidelines. *European Journal of Cancer*, 118, 10-34.

Schierbeck, J. et al. (2019). Skin cancer associated genodermatoses: a literature review. *Acta Dermato-Venereologica*, 99(4), 360-369.

Torrelo, A. et al. (2006). What syndrome is this? Bazex-Dupre-Christol syndrome. Pediatric Dermatology, 23(3), 286-290.

Tsao, A. S. et al. (2022). Phase II study of vismodegib in patients with SMO or PTCH1 mutated tumors: Results from NCI-MATCH ECOG-ACRIN Trial (EAY131) Subprotocol T. *American Society of Clinical Oncology*, Developmental Therapeutics—Molecularly Targeted Agents and Tumor Biology, 3010—Poster Discussion Session.

Wescott, R. et al. (2023). Sustained suppression of gorlin syndrome-associated basal cell carcinomas with vismodegib or sonidegib: a case series. *Current Oncology*, 30(10), 9156-9167.

Yang, X. H. et al. (2022). Inherited rare and common variants in PTCH1 and PTCH2 contributing to the predisposition to reproductive cancers. *Gene*, 814, 146157.

Zhang, H. et al. (2001). Role of PTCH and p53 genes in early-onset basal cell carcinoma. *The American Journal of Pathology*, 158(2), 381-385.

Bridgebio Pharma, Inc. (2021). BridgeBio Pharma, Inc. reports first quarter 2021 financial results and business update [Press release]. https://bridgebio.com/news/bridgebio-pharma-inc-reports-first-quarter-2021-financial-results-and-business-update/.

Johansen, E. M. (2021). Leo Pharma will not use acquisition option after candidate disappoints in phase III trial. MedWatch. https://medwatch.com/News/Pharma Biotech/article13281765.ece.

* cited by examiner

*Primary Examiner* — Kamal A Saeed
*Assistant Examiner* — Quincy Mckoy
(74) *Attorney, Agent, or Firm* — Baker Botts LLP

(57) ABSTRACT

Disclosed herein is a method of treatment and/or prevention basal cell carcinoma lesions, comprising topically administering a pharmaceutical composition comprising patidegib or a pharmaceutically acceptable salt thereof, to a subject in need thereof, wherein the subject has a genetic mutation PTCH.

11 Claims, 15 Drawing Sheets

TREATMENT AND PREVENTION OF BASAL CELL CARCINOMA WITH TOPICAL COMPOSITION COMPRISING PATIDEGIB

CROSS-REFERENCE TO RELATED APPLICATIONS

This application is a Continuation-in-Part of PCT International Application No. PCT/IL2024/050047, International Filing Date Jan. 11, 2024, claiming the benefit of U.S. Patent Application No. 63/438,543, filed Jan. 12, 2023, which are hereby incorporated by reference in their entirety.

FIELD OF THE INVENTION

The present invention, in some embodiments thereof, relates to a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH.

BACKGROUND

Basal cell carcinoma (BCC) is a common form of skin cancer, a subtype of Non Melanoma Skin Cancer (NMSC). BCC arises from abnormal, uncontrolled growth of basal cells, and is driven by the hedgehog (HH) signaling pathway which is considered to be a major signal transduction pathway during embryonic development, but it usually shuts down after birth. Activated Hedgehog (HH) signaling driven by mutations in the tumor-suppressor gene Patched (PTCH) and/or the G-protein-coupled receptor Smoothened (SMO) is known to promote oncogenic signaling and drives the growth of BCC. Mutations of the human patched gene such as PTCH1 and PTCH2 are associated with nevoid basal cell carcinoma syndrome and basal cell carcinoma. [1]

A variety of surgical and non-surgical therapies are available for BCCs. Nonsurgical therapies include radiation therapy, chemotherapy, and immunotherapy. These therapies can be useful for definitive treatment of primary tumors and some recurrent BCC tumors and for relieving symptoms associated with inoperable tumors. However, some of these therapies also can have significant unpleasant side effects. Side effects of radiation therapy and certain chemotherapies are well documented. One form of immunotherapy involves intralesional injections of interferon. While interferon therapy can be effective against BCC, the multiple intralesional injections can require several clinic visits per week for many weeks and are painful. There are antifungal agents, such as Itraconazole, that are known as Hh inhibitors. These agents inhibit the SMO in a different mechanism than patidegib and may reduce the size of BCC in general.

The most common topical treatment for BCC is 5-fluorouracil (5FU) and/or imiquimod, which are highly effective but causes a painful erosion in the treatment area.

There are genetic disorders which are associated with an increased risk of developing BCC at an early age and with increased morbidity. Such disorders include:

High Frequency BCC

High-frequency BCC (HF-BCC) often involves aggressive tumor behavior, frequent recurrence, and increased resistance to conventional therapies. This condition poses significant clinical and therapeutic challenges due to its persistent nature and potential resistance to standard treatments. A notable subgroup within high-frequency BCC includes individuals with Gorlin syndrome (also known as nevoid basal cell carcinoma syndrome).

- Nevoid basal cell carcinoma syndrome—Nevoid basal cell carcinoma syndrome (NBCCS), also known as basal cell nevus syndrome or Gorlin syndrome, is a rare multisystem disorder of autosomal dominant inheritance caused in most cases, not all, by germline mutations of the human patched gene-1 (PTCH1) and more rarely by mutation in SMO, SUFU (SUFU negative regulator of hedgehog signaling) and/or PTCH2 [1, 2a, 2b]. A subject that suffers from Gorlin syndrome does not necessarily have PTCH1. Vismodegib and Sonidegib are oral drugs, Hedgehog (Hh) pathway inhibitors, which are known to effect patients with Gorlin Syndrome, with and without PTCH1 mutation [3-5] therefore, do not require the confirmation of PTCH1 mutation before treatment.

Unlike these oral drugs, the inventors of this invention have surprisingly found, through a failed clinical trial (NCT No.: NCT3703310), involving Gorlin patients who were not required to have PTCH1 mutation, that in case of topical Hedgehog pathway inhibitor, patidegib, Gorlin patients must have a PTCH1 mutation in order for the treatment to be effective.

Affected patients have both developmental anomalies and postnatal tumors, including multiple BCCs, at an average age of 20 to 21 years, odontogenic keratocysts, and medulloblastoma [6]. Gorlin syndrome affects individuals which develop multiple (dozens to thousands) of microscopic and macroscopic BCCs, various benign hair follicle hamartomas, palmar, and plantar pits in addition to skeletal defects (bifid ribs and syndactyly), central nervous system abnormalities (calcification of the falx cerebri and agenesis of the corpus callosum), craniofacial features (enlarged skull, hypertelorism, and frontal bossing), and benign odontogenic keratocysts of the jaw.

- Rombo syndrome—Rombo syndrome was first described in a family with vermiculate atrophoderma and peripheral vasodilation with cyanosis in childhood, milia, trichoepitheliomas, hypotrichosis in adulthood, and BCCs developing in the third and fourth decade [7]. Rombo syndrome appears to be transmitted in a dominant pattern; however, a causative mutation had not been identified.
- Bazex-Dupré-Christol syndrome—Bazex-Dupré-Christol syndrome (also called Bazex syndrome or follicular atrophoderma and basal cell carcinomas) is an X-linked dominant disorder characterized by congenital hypotrichosis, follicular atrophoderma, milia, and multiple BCCs [8].
- Xeroderma pigmentosum—Xeroderma pigmentosum is a rare, autosomal recessive disorder due to mutations in any of eight genes involved in repair of UV-induced DNA damage [9]. Clinical findings include early-onset pigmentary skin changes and early development of skin cancers. SCCs and BCCs develop at an average age of nine years.
- Muir-Torre syndrome—Muir-Torre syndrome is a rare, autosomal dominant condition caused by mutations in DNA mismatch repair genes MLH1, MSH2, and MSH6. Patients present with sebaceous neoplasms, including sebaceous adenomas and carcinomas, keratoacanthomas, BCCs, and malignancies of the colon and genitourinary tract [7].
- Oculocutaneous albinism—Oculocutaneous albinism (OCA) is a group of autosomal recessive disorders of melanin biosynthesis presenting with a spectrum of visual disturbances and hypopigmentation of the skin and hair. Individuals with OCA have an increased risk of early-onset skin cancer, possibly by their teenage years. SCC is the most common type of cancer occurring in patients with OCA, but BCC and melanoma also occur [10].

BCC is observed in the general population typically on sun-exposed areas of the skin.

Further, an increased risk of developing BCCs exists for immunosuppression subjects or subjects that were exposed to radiation, asbestos, sun, or tanning salons. Thus, there remains a need for a non-surgical therapy for BCC that offers better treatment.

Patidegib

Patidegib compound also known in the art as "saridegib" and "IPI-926" has the following structure:

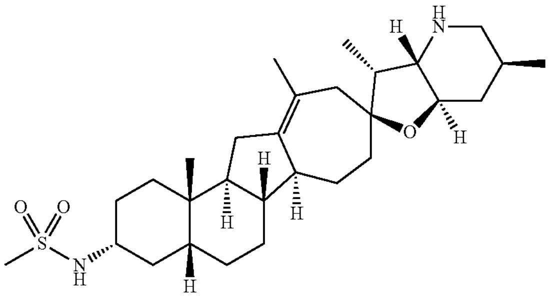

Patidegib is covered by U.S. Pat. No. 8,785,635 (US '635) entitled "Cyclopamine analogs". Patidegib is a member of a class of anti-cancer compounds known as hedgehog (HH) pathway inhibitors. Patidegib exhibits its pharmacological effect by inhibition of the G protein-coupled receptor smoothened, a component of the hedgehog (HH) signaling pathway.

REFERENCES

[1] Yang, Xin-Hua, et al. "Inherited rare and common variants in PTCH1 and PTCH2 contributing to the predisposition to reproductive cancers." *Gene* 814 (2022): 146157

[2a] Farndon P A, Del Mastro R G, Evans D G, Kilpatrick M W. Location of gene for Gorlin syndrome. Lancet 1992; 339:581.

[2b] Peris, K, et al. "Diagnosis and treatment of basal cell carcinoma: European consensus-based interdisciplinary guidelines." *European Journal of cancer* 118 (2019): 10-34. [3] MacDonald D S.

[3] Wescott, R., and Samlowski, W. "Sustained Suppression of Gorlin Syndrome-Associated Basal Cell Carcinomas with Vismodegib or Sonidegib: A Case Series." *Current Oncology* 30.10 (2023): 9156-9167.

[4] Khamaysi, Z., et al. "Segmental basal cell naevus syndrome caused by an activating mutation in smoothened." British Journal of Dermatology 175.1 (2016): 178-181.

[5] Tsao, Anne S., et al. "Phase II study of vismodegib in patients with SMO or PTCH1 mutated tumors: Results from NCI-MATCH ECOG-ACRIN Trial (EAY131) Subprotocol T." (2022): 3010-3010 (poster discussion session)

[6] A systematic review of the literature of nevoid basal cell carcinoma syndrome affecting East Asians and North Europeans. Oral Surg Oral Med Oral Pathol Oral Radiol 2015; 120:396.

[7] Schierbeck J, Vestergaard T, Bygum A. Skin Cancer Associated Genodermatoses: A Literature Review. Acta Derm Venereol 2019; 99:360.

[8] Torrelo A, Sprecher E, Mediero I G, et al. What syndrome is this? Bazex-Dupre-Christol syndrome. Pediatr Dermatol 2006; 23:286.

[9] DiGiovanna J J, Kraemer K H. Shining a light on xeroderma pigmentosum. J Invest Dermatol 2012; 132: 785.

[10] Kiprono S K, Chaula B M, Beltraminelli H. Histological review of skin cancers in African Albinos: a 10-year retrospective review. BMC Cancer 2014; 14:157.

SUMMARY OF THE INVENTION

The present invention is directed to a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject must have a genetic mutation PTCH1 and suffers from Gorlin syndrome.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
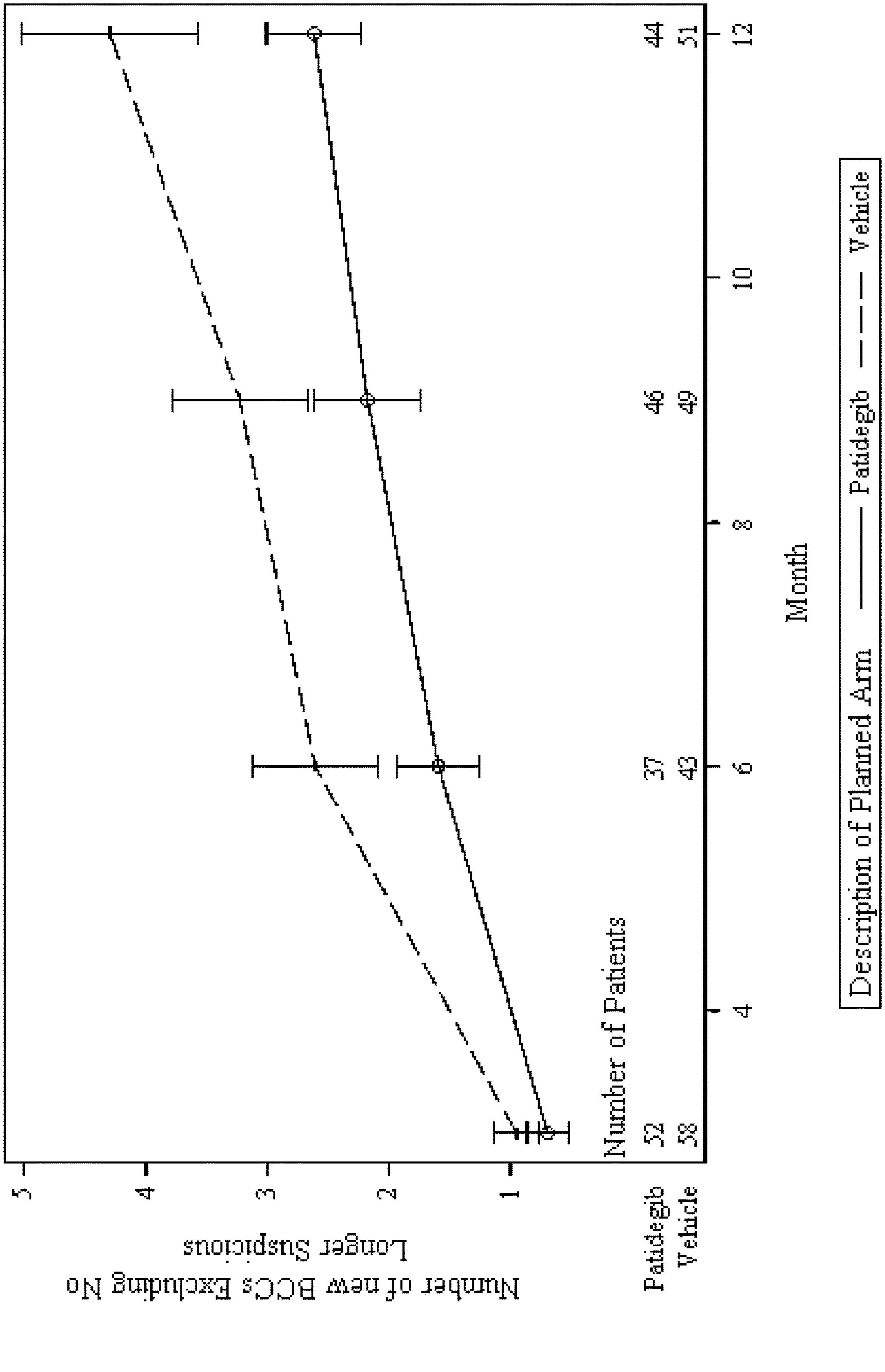
FIG. 1: Graphic illustration of number of new basal cell carcinoma (BCCs) lesions excluding no longer suspicious BCCs, observed, for subject suffering from PTCH1 mutation. Based on the study described in Example 2.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In some embodiments, the present invention is directed to a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1 and suffers from Gorlin syndrome.

In some embodiments, the present invention provides a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1 and suffers from Gorlin syndrome.

In some embodiments, the present invention provides a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein (i) the subject has at least 6 BCC lesions; or (ii) the subject has a genetic mutation; or (iii) the subject has at least 6 BCC lesions and a genetic mutation. In another embodiment the genetic mutation comprises PATCH1, PATCH2, SMO, SUFU or any combination thereof. In another embodiment, the subject has Gorlin syndrome.

In some embodiments, the present invention provides a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1 and suffers from Gorlin syndrome. In another embodiment, the subject has at least 6 BCC lesions and a genetic mutation PTCH1 and suffers from Gorlin syndrome. In another embodiment, said subject has at least 8 BCC lesions. In another embodiment, said subject has at least 10 BCC lesions. In another embodiment, said subject has at least 12 BCC lesions. In another embodiment, said subject must have at least 4 facial BCC lesions. In another embodiment, said subject has at least 6 facial BCC lesions. In another embodiment, said subject has at least 8 facial BCC lesions. In another embodiment, said subject has at least 10 facial BCC lesions. In another embodiment, said subject has at least 12 facial BCC lesions In some embodiments, the present invention provides a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein (i) the subject has at least 6 BCC lesions; or (ii) the subject has a genetic mutation PTCH; or (iii) the subject has at least 6 BCC lesions and a genetic mutation PTCH. In another embodiment, said PTCH is PTCH1. In another embodiment, said PTCH is PTCH2. In another embodiment, said PTCH is PTCH1 and/or PTCH2. In another embodiment, said subject must have at least 8 BCC lesions. In another embodiment, said subject must have at least 10 BCC lesions. In another embodiment, said subject has at least 12 BCC lesions. In another embodiment, said subject has at least 4 facial BCC lesions. In another embodiment, said subject has at least 6 facial BCC lesions. In another embodiment, said subject has at least 8 facial BCC lesions. In another embodiment, said subject has at least 10 facial BCC lesions. In another embodiment, said subject has at least 12 facial BCC lesions. In another embodiment, the subject has Gorlin syndrome.

In some embodiments, the present invention provides a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1 and suffers from Gorlin syndrome, and wherein the composition comprises patidegib in an amount of about 0.1% w/w to about 6% w/w. In another embodiment, the composition comprises patidegib in an amount of about 0.1-2% w/w, 0.1-3% w/w, 0.1-4% w/w, 0.1-5% w/w, 1-2% w/w, 1.5-3% w/w, 1-3% w/w, 1-4% w/w, 1-5% w/w, 2-4% w/w, 2-5% w/w, 2-6% w/w, or 0.1-6% w/w. In another embodiment, the composition comprises patidegib in an amount of about 1% w/w, 2% w/w, 3% w/w, 4% w/w, 5% w/w, or 6% w/w. In another embodiment, the composition comprises patidegib in an amount of about 2% w/w, 3% w/w, or 4% w/w. In another embodiment, the composition comprises patidegib in an amount of about 2%.

In some embodiments, provided herein is a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 BCC lesions; or (ii) a genetic mutation PTCH; or (iii) at least 6 BCC lesions and a genetic mutation PTCH, and wherein the composition comprises patidegib in an amount of about 0.1% w/w to about 6% w/w. In another embodiment, the composition comprises patidegib in an amount of about 0.1-2% w/w, 0.1-3% w/w, 0.1-4% w/w, 0.1-5% w/w, 1-2% w/w, 1.5-3% w/w, 1-3% w/w, 1-4% w/w, 1-5% w/w, 2-4% w/w, 2-5% w/w, 2-6% w/w, or 0.1-6% w/w. In another embodiment, the composition comprises patidegib in an amount of about 1% w/w, 2% w/w, 3% w/w, 4% w/w, 5% w/w, or 6% w/w. In another embodiment, the composition comprises patidegib in an amount of about 2% w/w, 3% w/w, or 4% w/w. In another embodiment, the composition comprises patidegib in an amount of about 2%.

In some embodiments, the present invention provides a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 facial BCC lesions; or (ii) a genetic mutation PTCH; or (iii) at least 6 BCC lesions and a genetic mutation PTCH.

In another embodiment, said PTCH is PTCH1. In another embodiment, said PTCH is PTCH2. In another embodiment, said PTCH is PTCH1 and/or PTCH2.

In another embodiment, said subject in the methods of this invention has at least 8 facial BCC lesions. In another embodiment, said subject has at least 10 facial BCC lesions. In another embodiment, said subject has at least 12 facial BCC lesions. In another embodiment, the subject has at least 8 BCC lesions and a genetic mutation PTCH. In another embodiment, the subject must has least 10 BCC lesions and a genetic mutation PTCH. In another embodiment, the subject has at least 12 BCC lesions and a genetic mutation PTCH.

In another embodiment, the subject in the methods of this invention has at least 6 facial BCC lesions and a genetic mutation PTCH. In another embodiment, the subject has at least 8 facial BCC lesions and a genetic mutation PTCH. In another embodiment, the subject has at least 10 facial BCC lesions and a genetic mutation PTCH. In another embodiment, the subject has at least 12 facial BCC lesions and a genetic mutation PTCH.

In some embodiments, provided herein is a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 facial BCC lesions; or (ii) a genetic mutation PTCH; or (iii) at least 6 BCC lesions and a genetic mutation PTCH, and wherein the composition comprises patidegib in an amount of about 0.1% w/w to about 6% w/w. In another embodiment, the composition comprises patidegib in an amount of about 0.1-2% w/w, 0.1-3% w/w, 0.1-4% w/w, 0.1-5% w/w, 1-2% w/w, 1.5-3% w/w, 1-3% w/w, 1-4% w/w, 1-5% w/w, 2-4% w/w, 2-5% w/w, 2-6% w/w, or 0.1-6% w/w. In another embodiment, the composition comprises patidegib in an amount of about 1% w/w, 2% w/w, 3% w/w, 4% w/w, 5% w/w, or 6% w/w. In another embodiment, the composition comprises patidegib in an amount of about 2% w/w, 3% w/w, or 4% w/w. In another embodiment, the composition comprises patidegib in an amount of about 2%.

In some embodiments, provided herein is a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 facial BCC lesions; or (ii) a genetic mutation PTCH; or (iii) at least 6 facial BCC lesions and a genetic mutation PTCH, and wherein the composition comprises patidegib in an amount of about 0.1% w/w to about 6% w/w. In another embodiment, the composition comprises patidegib in an amount of about 0.1-2% w/w, 0.1-3% w/w, 0.1-4% w/w, 0.1-5% w/w, 1-2% w/w, 1.5-3% w/w, 1-3% w/w, 1-4% w/w, 1-5% w/w, 2-4% w/w, 2-5% w/w, 2-6% w/w, or 0.1-6% w/w. In another embodiment, the composition comprises patidegib in an amount of about 1% w/w, 2% w/w, 3% w/w, 4% w/w, 5% w/w, or 6% w/w. In another embodiment, the composition comprises patidegib in an amount of about 2% w/w, 3% w/w, or 4% w/w. In another embodiment, the composition comprises patidegib in an amount of about 2%.

In some embodiments, the present invention provides a method of treatment and/or prevention of basal cell carcinoma (BCC) lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1 and suffers from Gorlin syndrome, and the composition comprises patidegib in an amount of about 2% w/w.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 facial BCC lesions; or (ii) a genetic mutation PTCH; or (iii) at least 6 BCC lesions and a genetic mutation PTCH, and wherein the composition comprises patidegib in an amount of about 2% w/w.

In some embodiments, the patidegib composition of this invention is selected from a cream, an ointment, a gel, a lotion, a spray, a patch or a foam. In some embodiments, the topical composition of patidegib of this invention is a gel. In some embodiments, the topical composition of patidegib of this invention is a cream.

In another embodiment, the patidegib is formulated as a gel formulation. In another embodiment, the patidegib is formulated as a cream formulation.

In some embodiments, provided herein is a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1 and suffers from Gorlin syndrome, and wherein the patidegib is formulated as a gel or a cream formulation. In another embodiment, the patidegib is formulated as a gel formulation.

In some embodiments, provided herein is a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject must have a genetic mutation PTCH1 and suffers from Gorlin syndrome, and wherein the patidegib is formulated as a gel or a cream formulation. In another embodiment, the patidegib is formulated as a gel as shown in Example 1.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject eligible for the treatment and/or prevention is selected according to any one of the following criteria (i) the subject has at least 6 facial BCC lesions; or (ii) the subject has a genetic mutation PTCH; or (iii) the subject has at least 6 BCC lesions and a genetic mutation PTCH, and wherein the patidegib is in an amount of about 0.1% w/w to about 6% w/w, and wherein the patidegib is formulated as a gel formulation. In another embodiment, the patidegib is formulated as shown in Example 1.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 BCC lesions.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 facial BCC lesions.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has a genetic mutation PTCH.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 BCC lesions and a genetic mutation PTCH.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 facial BCC lesions and a genetic mutation PTCH.

In some embodiments, provided herein is a method of treatment of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 BCC lesions; or (ii) a genetic mutation PTCH; or (iii) at least 6 BCC lesions and a genetic mutation PTCH.

In some embodiments, provided herein is a method of treatment of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 facial BCC lesions; or (ii) a genetic mutation PTCH; or (iii) at least 6 BCC lesions and a genetic mutation PTCH. In some embodiments, provided herein is a method of treatment of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 facial BCC lesions; or (ii) a genetic mutation PTCH; or (iii) at least 6 facial BCC lesions and a genetic mutation PTCH.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least one of the following (i) the at least 6 BCC lesions; or (ii) a genetic mutation PTCH; or (iii) at least 6 BCC lesions and a genetic mutation PTCH, and wherein said subject suffers from Gorlin syndrome. In another embodiment, the subject has at least 6 facial lesions. In another embodiment, the subject has a genetic mutation PTCH. In another embodiment, the subject has at least 6 facial BCC lesions and a genetic mutation PTCH.

In some embodiments, provided herein is a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH and suffers from Gorlin syndrome. In some embodiments, provided herein is a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH and suffers from Gorlin syndrome, and wherein the method would not be effective on Gorlin subject that does not have a genetic mutation PTCH. In another embodiment, the subject has at least 6 BCC lesions. In another embodiment, the subject has at least 10 BCC lesions.

In some embodiments, provided herein is a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1 and suffers from Gorlin syndrome. In another embodiment, the method would not be effective on Gorlin subject that does not have a genetic mutation PTCH1 as shown in Example 4.

In another embodiment, the method would not prevent formation of new BCCs on Gorlin subject that does not have a genetic mutation PTCH1 as shown in Example 4. In another embodiment, the method does not reduce the number of qualifying nSEBs on Gorlin subject that does not have a genetic mutation PTCH1 as shown in Example 4.

In some embodiments, provided herein is a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject must have a genetic mutation PTCH1 and suffers from Gorlin syndrome, and wherein the method would not be effective on Gorlin subject that does not have a genetic mutation PTCH1. In another embodiment, the subject has at least 6 BCC lesions. In another embodiment, the subject has at least 10 BCC lesions.

In some embodiments, provided herein is a method of treatment and/or prevention of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject must have a genetic mutation PTCH1, suffers from Gorlin syndrome, and has at least 6 BCC lesions. In another embodiment, the subject has at least 10 BCC lesions.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 BCC lesions and wherein said subject suffers from Gorlin syndrome.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 facial BCC lesions, and wherein said subject suffers from Gorlin syndrome.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject must have a genetic mutation PTCH and wherein said subject suffers from Gorlin syndrome.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 BCC lesions and a genetic mutation PTCH and wherein said subject suffers from Gorlin syndrome.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 facial BCC lesions and a genetic mutation PTCH and wherein said subject suffers from Gorlin syndrome.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 BCC lesions, and wherein said subject suffers from immunosuppression or said subject was exposed to radiation, asbestos, sun, or tanning salons. In another embodiment, the subject has at least 8 BCC lesions. In another embodiment, the subject has at least 10 BCC lesions. In another embodiment, the subject has at least 12 BCC lesions. In another embodiment, the subject has at least 6 facial BCC lesions. In another embodiment, the subject has at least 8 facial BCC lesions. In another embodiment, the subject must has at least 10 facial BCC lesions. In another embodiment, the subject has at least 12 facial BCC lesions.

In some embodiments, provided herein is a method of treatment and/or prevention of basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 facial BCC lesions, and wherein said subject suffers from immunosuppression or said subject was exposed to radiation, asbestos, sun, or tanning salons.

In some embodiments, provided herein is a method of treatment and/or prevention basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 BCC lesions, and wherein said subject suffers from a disorder comprising of non-melanoma skin cancer, Rombo syndrome, Bazex-Dupré-Christol syndrome, Xeroderma pigmentosum, Muir-Torre syndrome, Oculocutaneous albinism, or Gorlin syndrome.

In some embodiments, provided herein is a method of treatment and/or prevention basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 facial BCC lesions, and wherein said subject suffers from a disorder comprising of non-melanoma skin cancer, Rombo syndrome, Bazex-Dupré-Christol syndrome, Xeroderma pigmentosum, Muir-Torre syndrome, Oculocutaneous albinism, or Gorlin syndrome.

In some embodiments, provided herein is a method of treatment and/or prevention basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 BCC lesions, and wherein said subject suffers from Rombo syndrome, Bazex-Dupré-Christol syndrome, Xeroderma pigmentosum, Muir-Torre syndrome, or Oculocutaneous albinism.

In some embodiments, provided herein is a method of treatment and/or prevention basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least 6 facial BCC lesions, and wherein said subject suffers from Rombo syndrome, Bazex-Dupré-Christol syndrome, Xeroderma pigmentosum, Muir-Torre syndrome, or Oculocutaneous albinism.

In some embodiments, provided herein is a method of treatment of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1, suffers from Gorlin syndrome, and wherein the method of treatment basal cell carcinoma results in a reduction of BBC lesion size or resolved BBC lesion over time.

In some embodiments, provided herein is a method of treatment of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1, suffers from Gorlin syndrome, and wherein the method resolves and or reduce the size of surgically eligible BCCs.

In some embodiments, the method of this invention of treatment BCC resulting in a reduction of BCC lesion size or clinically resolved over time. In another embodiment, the method of this invention of treatment BCC resulting in a reduction of BCC lesion size. In another embodiment, the BCC lesion size is reduced by about 1-100%. In another embodiment, the lesion size is reduced by about 5%. In another embodiment, the BCC lesion size is reduced by about 10%. In another embodiment, the BCC lesion size is reduced by about 20%. In another embodiment, the lesion size is reduced by about 30%. In another embodiment, the lesion size is reduced by about 40%. In another embodiment, the lesion size is reduced by about 50%. In another embodiment, the BCC lesion size is reduced by about 60%. In another embodiment, the BCC lesion size is reduced by about 70%. In another embodiment, the lesion size is reduced by about 75%. In another embodiment, the BCC lesion size is reduced by about 80%. In another embodiment, the BCC lesion size is reduced by about 85%. In another embodiment, the BCC lesion size is reduced by about 90%. In another embodiment, the BCC lesion size is reduced by about 95%. In another embodiment, the BCC lesion size is reduced by about 100%.

In another embodiment, the treatment of BCC results in resolved BCC, particularly the BCC disappeared completely. In another embodiment, the treatment of BCC lesion results in resolved BCC, wherein the lesion is no longer suspected as BCC.

In some embodiments, the method of this invention prevents formation of new BCC, wherein the subject has at least one of the following (i) at least 6 BCC lesions; or (ii) a genetic mutation PTCH; or (iii) at least 6 BCC lesions and a genetic mutation PTCH. In another embodiment, the subject has at least 6 facial BCC lesions. In another embodiment, the subject has at least 6 facial BCC lesions and a genetic mutation PTCH.

In some embodiments, the method of this invention prevents formation of nSEBs, wherein the subject has at least one of the following (i) at least 6 BCC lesions; or (ii) a genetic mutation PTCH; or (iii) at least 6 BCC lesions and a genetic mutation PTCH. In another embodiment, the subject has at least 6 facial BCC lesions and a genetic mutation PTCH. In another embodiment, the subject has at least 6 facial BCC lesions. In another embodiment, the subject has at least 6 facial BCC lesions and a genetic mutation PTCH.

In some embodiments, provided herein is a method of treatment of basal cell carcinoma lesions, comprising topically administering a pharmaceutical composition comprising patidegib or a pharmaceutically acceptable salt thereof, and a pharmaceutically acceptable carrier, to a subject in need thereof, wherein the subject has a genetic mutation PTCH1, suffers from Gorlin syndrome, and wherein prevention basal cell carcinoma lesions refers to preventing formation of new BCCs, or new surgically eligible BCCs.

In some embodiments, the method of this invention reduces the number of nSEBs, wherein the subject has at least one of the following (i) at least 6 BCC lesions; or (ii) a genetic mutation PTCH; or (iii) at least 6 BCC lesions and a genetic mutation PTCH. In another embodiment, the subject has at least 6 facial BCC lesions. In another embodiment, the subject has at least 6 facial BCC lesions and a genetic mutation PTCH. In another embodiment, the subject has a genetic mutation PTCH1, suffers from Gorlin syndrome.

In some embodiments, the present invention provides a method of treatment and/or prevention basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 BCC lesions; or (ii) a genetic mutation PTCH; or (iii). at least 6 BCC lesions and a genetic mutation PTCH; wherein the composition is topically administered once daily, twice daily, trice daily, every other day, once a week, twice a week, or three times a week. In another embodiment, the subject has a genetic mutation PTCH1, suffers from Gorlin syndrome.

In some embodiments, the present invention provides a method of treatment and/or prevention basal cell carcinoma (BCC), comprising topically administering a pharmaceutical composition comprising patidegib or a pharmaceutically acceptable salt thereof, and a pharmaceutically acceptable carrier, to a subject in need thereof, wherein the subject has at least one of the following (i) at least 6 facial BCC lesions; or (ii) a genetic mutation PTCH; or (iii) at least 6 BCC lesions and a genetic mutation PTCH; wherein the composition is topically administered once daily, twice daily, trice daily, every other day, once a week, twice a week, or three times a week. In another embodiment, the subject must have at least 6 facial BCC lesions and a genetic mutation PTCH. In another embodiment, the subject has a genetic mutation PTCH1, suffers from Gorlin syndrome.

In some embodiments, provided herein is a method of treatment and/or prevention comprising once daily, twice daily, trice daily, every other day, once a week, twice a week, or three times a week topical application of therapeutically effective amounts of a composition comprising patidegib or a pharmaceutically acceptable salt thereof.

In some embodiments, provided herein is a method of treatment and/or prevention of BCC comprising once daily, twice daily, trice daily, every other day, once a week, twice a week, or three times a week topical application of therapeutically effective amounts of a composition comprising patidegib or a pharmaceutically acceptable salt thereof, to the facial skin of the subject in need thereof until said BCC is cured, prevented or alleviated or according to doctor's instructions, wherein the subject has a genetic mutation PTCH1, suffers from Gorlin syndrome.

In some embodiments, provided herein is a method of treatment and/or prevention of BCC comprising once daily, twice daily, trice daily, every other day, once a week, twice a week, or three times a week topical application of therapeutically effective amounts of a composition comprising patidegib or a pharmaceutically acceptable salt thereof, to the facial skin of the subject in need thereof until said BCC is cured, prevented or alleviated or according to doctor's instructions, and wherein the subject has one of the following (i) at least 6 facial BCC lesions; or (ii) genetic mutation PTCH; or (iii) at least 6 BCC lesions and a genetic mutation PTCH. In another embodiment, the subject has at least 6 facial BCC lesions and a genetic mutation PTCH.

In some embodiments, provided herein is a method of treatment and/or prevention of BCC comprising once daily, twice daily, trice daily, every other day, once a week, twice a week, or three times a week topical application of therapeutically effective amounts of the composition described herein to affected skin area of the subject in need thereof until said BCC is cured, prevented or alleviated or according to doctor's instructions, and wherein the subject at least one of the following (i) at least 6 BCC lesions; or (ii) a genetic mutation PTCH; or (iii) the subject has at least 6 BCC lesions and a genetic mutation PTCH. In another embodiment, the subject has at least 6 facial BCC lesions. In another embodiment, the subject has at least 6 facial BCC lesions and a genetic mutation PTCH.

In some embodiments, provided herein is a method of treatment and/or prevention of BCC comprising once daily, twice daily, trice daily, every other day, once a week, twice a week, or three times a week topical application of therapeutically effective amounts of the composition described herein to affected skin area of the subject in need thereof until said BCC is cured, prevented or alleviated or according to doctor's instructions, and wherein the subject has at least one of the following (i) at least 6 facial BCC lesions; or (ii) a genetic mutation PTCH; or (iii) at least 6 BCC lesions and a genetic mutation PTCH. In another embodiment, the subject has at least 6 facial BCC lesions and a genetic mutation PTCH.

In some embodiments, provided herein is a method of treatment and/or prevention of BCC comprising once daily, twice daily, trice daily, every other day, once a week, twice a week, or three times a week topical application of therapeutically effective amounts of the composition described herein to any area of the body of the subject in need thereof until said BCC is cured, prevented or alleviated or according to doctor's instructions, and wherein the subject has at least one of the following (i) at least 6 BCC lesions; or (ii) a genetic mutation PTCH; or (iii) at least 6 BCC lesions and a genetic mutation PTCH. In another embodiment, the subject has at least 6 facial BCC lesions. In another embodiment, the subject has at least 6 facial BCC lesions and a genetic mutation PTCH.

In some embodiments, provided herein is a method of treatment and/or prevention of BCC comprising once daily, twice daily, trice daily, every other day, once a week, twice a week, or three times a week topical application of therapeutically effective amounts of the said composition to the entire body of the subject in need thereof until said BCC is cured, prevented or alleviated or according to doctor's instructions, and wherein the subject has at least one of the following (i) at least 6 BCC lesions; or (ii) a genetic mutation PTCH; or (iii) at least 6 BCC lesions and a genetic mutation PTCH. In another embodiment, the subject has at least 6 facial BCC lesions. In another embodiment, the subject has at least 6 facial BCC lesions and a genetic mutation PTCH.

In some embodiments, provided herein is a method of treatment of BCC lesions comprising once daily, twice daily, trice daily, every other day, trice daily, every other day, once a week, twice a week, or three times a week topical application of therapeutically effective amounts of the said composition on the BCC lesion of the subject in need thereof until said BCC is cured, prevented or alleviated or according to doctor's instructions, and wherein (i) the subject has at least 6 BCC lesions; or (ii) the subject has a genetic mutation PTCH; or (iii) the subject has at least 6 BCC lesions and a genetic mutation PTCH. In another embodiment the subject has a genetic mutation PTCH1 and suffers from Gorlin syndrome.

In some embodiments, provided herein is a method of treatment and/or prevention of BCC lesions comprising once daily, twice daily, trice daily, every other day, trice daily, every other day, once a week, twice a week, or three times a week topical application of therapeutically effective amounts of the said composition on the BCC lesion and on the skin surrounding the BCC lesion of the subject in need thereof until said BCC is cured, prevented or alleviated or according to doctor's instructions, and wherein (i) the subject has at least 6 BCC lesions; or (ii) the subject has a genetic mutation PTCH; or (iii) the subject must have at least 6 facial BCC lesions and a genetic mutation PTCH. In another embodiment, the subject has at least 6 facial BCC lesions. In another embodiment, the subject has at least 6 facial BCC lesions and a genetic mutation PTCH.

In some embodiments, provided herein is a method of treatment of BCC lesions comprising once daily, twice daily, trice daily, every other day, trice daily, every other day, once a week, twice a week, or three times a week topical application of therapeutically effective amounts of the said composition on the BCC lesion of the subject in need thereof until said BCC is cured, prevented or alleviated or according to doctor's instructions, and wherein the subject has (i) at least 6 facial BCC lesions; or (ii) a genetic mutation PTCH; or (iii) at least 6 facial BCC lesions and a genetic mutation PTCH. In another embodiment the subject has a genetic mutation PTCH1 and suffers from Gorlin syndrome.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the composition is topically administered for a period of about 3 months, about 6 months, about 9 months, about 12 months, about 18 months, about 24 months, about 36 months, chronically or for a lifetime; and wherein (i) the subject has at least 6 BCC lesions; or (ii) the subject has a genetic mutation PTCH; or (iii) the subject has at least 6 BCC lesions and a genetic mutation PTCH. Each represents a separate embodiment of this invention. In another embodiment, the subject has at least 6 facial BCC lesions. In another embodiment, the subject has at least 6 facial BCC lesions and a genetic mutation PTCH. In another embodiment the subject has a genetic mutation PTCH1 and suffers from Gorlin syndrome.

In another embodiment, the composition is topically administered for a period of about 3 months. In another embodiment, the composition is topically administered for a period of about 6 months. In another embodiment, the composition is topically administered for a period of about 9 months. In another embodiment, the composition is topically administered for a period of about 12 months. In another embodiment, the composition is topically administered for a period of more than 12 months. In another embodiment, the composition is topically administered for a period of a lifetime. In another embodiment, the composition is topically administered chronically.

In some embodiments, provided herein is a method of treatment and/or prevention of BCC comprising topically administering a pharmaceutical composition comprising patidegib or a pharmaceutically acceptable salt thereof, and a pharmaceutically acceptable carrier, to a subject in need thereof, wherein the composition is administered for a period of administration of more than 12 months, more than 18 months, more than 24 months, more than 36 months, at least 1-10 years, more than 1 year, more than 2 years, more than 3 years, more than 4 years, more than 5 years, more than 6 years, more than 7 years, more than 8 years, more than 9 years, more than 10 years, or chronically, or for a lifetime; and wherein the subject has at least one of the following (i) at least 6 BCC lesions; or (ii) a genetic mutation PTCH; or (iii) at least 6 BCC lesions and a genetic mutation PTCH. Each represents a separate embodiment of this invention. In another embodiment, the subject has at least 6 facial BCC lesions. In another embodiment, the subject has at least 6 facial BCC lesions and a genetic mutation PTCH. In another embodiment, the subject does not develop drug resistance. In another embodiment, the subject does not develop drug resistance following a discontinuation period of administration during the treatment. In another embodiment the subject has a genetic mutation PTCH1 and suffers from Gorlin syndrome.

In some embodiment, the subject of the methods provided in this invention does not develop drug resistance. In another embodiment, the subject of the methods provided in this invention does not develop drug resistance following a discontinuation period of administration during the treatment.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the composition is topically administered for a period of more than 12 months; wherein the subject has at least one of the following (i) at least 6 BCC lesions; or (ii) a genetic mutation PTCH; or (iii) at least 6 BCC lesions and a genetic mutation PTCH; and wherein said subject does not develop drug resistance. Each represents a separate embodiment for this invention. In another embodiment, the composition is administered for a period of more than 18 months. In another embodiment, the composition is administered for a period of more than 24 months. In another embodiment, the composition is administered for a period of a lifetime. In another embodiment, the composition is administered chronically. In another embodiment, the subject must have at least 6 facial BCC lesions. In another embodiment, the subject must have at least 6 facial BCC lesions and a genetic mutation PTCH. In another embodiment, the subject does not develop drug resistance following a discontinuation period of administration during the treatment. In another embodiment the subject has a genetic mutation PTCH1 and suffers from Gorlin syndrome. In some embodiments, provided herein a method of treatment and/or prevention of basal cell carcinoma, comprising topically administering a pharmaceutical composition comprising patidegib or a pharmaceutically acceptable salt thereof, and a pharmaceutically acceptable carrier, to a subject wherein the subject has at least one of the following (i) at least 6 BCC lesions; or (ii) a genetic mutation PTCH; or (iii) at least 6 BCC lesions and a genetic mutation PTCH, wherein the subject does not develop drug resistance. In another embodiment, wherein the subject does not develop drug resistance following a discontinuation period of administration during the treatment. In some embodiments, the period of administration of the methods of this invention does not affect the drug efficacy. In another embodiment, following a discontinuation period of administration during the treatment, the drug efficacy is not affected. In another embodiment the subject has a genetic mutation PTCH1 and suffers from Gorlin syndrome.

In some embodiments, provided herein a method of treatment and/or prevention of basal cell carcinoma, comprising topically administering a pharmaceutical composition comprising patidegib or a pharmaceutically acceptable salt thereof, and a pharmaceutically acceptable carrier, to a subject wherein (i) the subject has at least 6 facial BCC lesions; or (ii) the subject has a genetic mutation PTCH; or (iii) the subject has at least 6 BCC lesions and a genetic mutation PTCH, and wherein following a discontinuation period of administration during the treatment, the drug efficacy is not affected. In another embodiment the subject has a genetic mutation PTCH1 and suffers from Gorlin syndrome.

In some embodiments, the methods provided herein, the period of administration comprises at least consecutive 12 months of administration.

In some embodiments, the methods provided herein, the period of administration comprises (i) consecutive 12 months of administration (ii) followed by a discontinuation period (iii) followed by continuation of administration, wherein drug efficacy is not affected by the discontinuation period of administration during the treatment. In another embodiment, the discontinuation period is of 1, 2, 3, 4, 5, 6, 7, 8 months or between 1-3 months, 1-24 months, between 2-12 months, between 3-12 months, between 3-8 months, between 3-10 months.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the composition is topically administered for a period of at least 9 months, wherein after 9 months of administration the efficacy in treating and/or preventing of BCC is improved in comparison to the administration of the vehicle, and wherein (i) the subject has at least 6 BCC lesions; or (ii) the subject has a genetic mutation PTCH; or (iii) the subject has at least 6 BCC lesions and a genetic mutation PTCH. In another embodiment, the subject must have at least 6 facial BCC lesions. In another embodiment, the subject must have at least 6 facial BCC lesions and a genetic mutation PTCH. In another embodiment the subject has a genetic mutation PTCH1 and suffers from Gorlin syndrome.

In some embodiments, provided herein is a method of treatment of resolving SEB comprising topically administered a pharmaceutical composition comprising patidegib or a pharmaceutically acceptable salt thereof, and a pharmaceutically acceptable carrier, to a subject in need thereof, wherein the composition is topically administered for a period of at least 9 months, wherein after 9 months of administration the efficacy in treating and/or preventing of BCC is improved in comparison to the administration of the vehicle, and wherein the subject has at least one of the following (i) at least 6 BCC lesions; or (ii) a genetic mutation PTCH; or (iii) at least 6 BCC lesions and a genetic mutation PTCH. In another embodiment, the subject has at least 6 facial BCC lesions. In another embodiment, the subject has at least 6 facial BCC lesions and a genetic mutation PTCH. In another embodiment the subject has a genetic mutation PTCH1 and suffers from Gorlin syndrome.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the composition is topically administered for a period of more than 12 months, wherein after 12 months of administration the efficacy in treating and/or preventing of BCC is improved in comparison to the administration of the vehicle, and wherein (i) the subject has at least 6 BCC lesions; or (ii) the subject has a genetic mutation PTCH; or (iii) the subject has at least 6 BCC lesions and a genetic mutation PTCH. In another embodiment, the subject has at least 6 facial BCC lesions. In another embodiment, the subject has at least 6 facial BCC lesions and a genetic mutation PTCH. In another embodiment the subject has a genetic mutation PTCH1 and suffers from Gorlin syndrome.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the composition is topically administered for a period of at least 12 months, wherein after 12 months of administration the efficacy in treating and/or preventing of BCC is not affected in comparison to the efficacy in treating/preventing in the first 12 months of topically administered a pharmaceutical composition comprising patidegib or a pharmaceutically acceptable salt thereof, and a pharmaceutically acceptable carrier, and wherein (i) the subject has at least 6 BCC lesions; or (ii) the subject has a genetic mutation PTCH; or (iii) the subject has at least 6 BCC lesions and a genetic mutation PTCH. In another embodiment, the subject has at least 6 facial BCC lesions. In another embodiment, the subject has at least 6 facial BCC lesions and a genetic mutation PTCH.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the composition is topically administered for a period of at least 18 months, wherein after 18 months of administration the efficacy in treating and/or preventing of BCC is not affected, and wherein (i) the subject has at least 6 BCC lesions; or (ii) the subject has a genetic mutation PTCH; or (iii) the subject has at least 6 BCC lesions and a genetic mutation PTCH. In another embodiment the subject has a genetic mutation PTCH1 and suffers from Gorlin syndrome.

In another embodiment, the subject must have at least 6 facial BCC lesions. In another embodiment, the subject must have at least 6 facial BCC lesions and a genetic mutation PTCH.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the composition is topically administered for a period of about 3 months, about 6 months, about 9 months, about 12 months, chronically, or for a lifetime; and wherein (i) the subject must have at least 6 facial BCC lesions; or (ii) the subject must have a genetic mutation PTCH; or (iii) the subject must have at least 6 BCC lesions and a genetic mutation PTCH. In another embodiment the subject has a genetic mutation PTCH1 and suffers from Gorlin syndrome.

In some embodiments, provided herein is a method of treatment and/or prevention of BCC comprising topically administered a pharmaceutical composition comprising patidegib or a pharmaceutically acceptable salt thereof, and a pharmaceutically acceptable carrier, to a subject in need thereof, wherein the number BCC surgeries is reduced; and wherein (i) the subject must have at least 6 BCC lesions; or (ii) the subject must have a genetic mutation PTCH; or (iii) the subject must have at least 6 BCC lesions and a genetic mutation PTCH. In another embodiment, the BCC surgeries is reduced following 12 months of treatment (Example 2, Table 14). In another embodiment the subject has a genetic mutation PTCH1 and suffers from Gorlin syndrome.

In some embodiments, the pharmaceutically acceptable carrier of the composition of this invention comprises DGME (diethylene glycol monoethyl ether), HPC (hydroxypropyl cellulose), borate buffer, dehydrated alcohol, propylene glycol, phenoxyethanol, or any combination thereof. In another embodiment, the pharmaceutically acceptable carrier of the composition of this invention encompasses carriers, excipients, and diluents, meaning a material, composition or vehicle, such as a liquid or solid filler, diluent, excipient, solvent or encapsulating material involved in carrying or transporting a pharmaceutical agent across the stratum corneum.

In some embodiments, the method of this invention comprises topically applying a composition comprising patidegib, or a pharmaceutically acceptable salt thereof, and a pharmaceutically acceptable carrier.

In another embodiment, the patidegib, or a pharmaceutically acceptable salt thereof compound can be formulated with any pharmaceutically acceptable carrier, and may be a liquid, semi-solid or solid composition. Pharmaceutical and cosmetic carriers or vehicles suitable for topical administration of the compositions to the skin or mucosa are known to those skilled in the art and the patidegib compound can be included in the carrier in an amount sufficient to provide a therapeutically useful effect in the treatment and/or prevention of BCC. In one embodiment, the composition comprising patidegib, or a pharmaceutically acceptable salt thereof, is a liquid. Liquid dosage forms for topical administration include emulsions, solutions and suspensions containing diluents commonly used in the art, such as alcohols, glycols, oils, water and the like. The compositions may also include wetting agents, emulsifying and suspending agents.

The composition may be in the form of solutions, suspensions, emulsions, ointments, lotions, gels, and the like. Emulsions of the form oil-in-water or water-in-oil are contemplated. Gels are formed by the entrapment of large amounts of aqueous or aqueous-alcoholic liquids in a network of polymers or of colloidal solid particles. Such polymers or colloids are typically present at concentrations of less than 10% w/w and are also referred to as gelling agents or thickening agents. Examples of suitable gelling agents include carboxymethyl cellulose, hydroxypropylmethyl cellulose, hydroxyethyl cellulose, hydroxypropyl cellulose, methyl cellulose, sodium alginate, alginic acid, pectin, tragacanth, carrageen, agar, clays, aluminum silicate, carbomers, etc.

Creams and ointments may also be utilized. They are emulsions of oleaginous substances and water (i.e. the carrier). The cream may be a water-in-oil (w/o) in which an aqueous phase is dispersed in an oil phase, or an oil-in-water (o/w) which has an oil dispersed within an aqueous base. An ointment is also contemplated and is typically more viscous than an oil-in-water cream. Traditional ointment bases (i.e. the carrier) include hydrocarbons (petrolatum, beeswax, etc.) vegetable oils, fatty alcohols (cholesterol, lanolin, wool alcohol, stearyl alcohol, etc.) or silicones. Pastes are a type of ointment into which a high percentage of insoluble particulate solids have been added, up to 50% by weight. Insoluble solids such as starch, zinc oxide, calcium carbonate, or talc may be used.

Aerosols may also be utilized. The compound may be dissolved in a propellant and a co-solvent such ethanol, acetone, hexadecyl alcohol, etc. Foaming agents may be incorporated to produce a mousse.

Emollient or lubricating vehicles that help hydrate the skin can also be used. Examples of suitable bases or vehicles for preparing hydrating compositions for use with human skin are petrolatum, petrolatum plus volatile silicones, lanolin, cold cream (USP), and hydrophilic ointment (USP).

A wide variety of methods may be used for preparing the formulations described above. Broadly speaking, the formulations may be prepared by combining together the components of the formulation, as described herein, at a temperature and for a time sufficient to provide a pharmaceutically acceptable composition. The term "combining together", as used herein, means that all of the components of the compositions may be combined and mixed together at about the same time. The term "combining together" also means that the various components may be combined in one or more sequences to provide the desired product. The formulation can be prepared on a weight/weight (w/w) or a weight/volume (w/v) basis depending upon the form of the final dosage form.

The composition comprises a weight fraction of patidegib or a pharmaceutically acceptable salt thereof, that may be dissolved, suspended, dispersed or otherwise mixed in a selected carrier or vehicle, at an effective concentration such that the pruritic condition is relieved or ameliorated. Compositions that are in solution form and intended for topical administration may contain an amount of patidegib or a pharmaceutically acceptable salt thereof, between about 0.1% w/w to about 6% w/w, with the balance of the solution being water, a suitable organic solvent or other suitable solvent or buffer. Compositions that are formulated as solutions, emulsions, or suspensions can be applied to the skin, or can be formulated as an aerosol or foam and applied to the skin as a spray-on. The aerosol compositions typically contain from 25% to 80% w/w, preferably from 30% to 50% w/w, of a suitable propellant.

Compositions of solid forms intended for topical application can be formulated as stick-type compositions intended for application to the lips or other parts of the body. Such compositions contain an effective amount of patidegib or a pharmaceutically acceptable salt thereof. The amount of the petidegib compound is typically from about 0.1% w/w to about 6% w/w. The solid form of the composition may also contain from about 40% to 98% w/w, preferably from about 50% to 90% w/w, of carrier(s).

The term "pharmaceutically acceptable salt" as used herein refers to a commonly used salts to form alkali metal salts of free acids and to form addition salts of free bases. The nature of the salt is not critical, provided that it is pharmaceutically acceptable. The term "pharmaceutically acceptable salts" also includes solvates of addition salts, such as hydrates, as well as polymorphs of addition salts. Suitable pharmaceutically acceptable acid addition salts can be prepared from an inorganic acid or from an organic acid. Examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric and galacturonic acid.

The term "genetic mutation PTCH" refers to genetic mutation PTCH1 and/or genetic mutation PTCH2.

The term "treatment of BCC" refers to treating BCC including surgically eligible BCC until BCC is disappeared completely or reducing lesion growth (e.g. decrease of the size of a lesion/tumor). Moreover, "treatment of BCC" refers to treatment of BCC found on the entire body of the subject. In other embodiment, the term "treatment of BCC" refers to treating BCC including surgically eligible BCC until BCC is disappeared completely or reducing lesion growth (e.g. decrease of the size of a lesion/tumor) wherein the subject (i) has or must have at least 6 facial BCC lesions at baseline, before treatment; or (ii) the subject has or must have a genetic mutation PTCH; or (iii) the subject has or must have at least 6 BCC lesions at baseline, as baseline before treatment and a genetic mutation PTCH. In other embodiment, the term "treatment of BCC" refers to treating BCC including surgically eligible BCC until BCC is disappeared completely or reducing lesion growth (e.g. decrease of the size of a lesion/tumor) wherein the subject (i) has or must have at least 6 facial BCC lesions at baseline, before treatment; or (ii) the subject has or must have a genetic mutation PTCH; or (iii) the subject has or must have at least 6 facial BCC lesions at baseline, before treatment and a genetic mutation PTCH. In another embodiment the subject has or must have a genetic mutation PTCH1 and suffers from Gorlin syndrome.

The term "prevention of BCC" refers to preventing development of new BCC and new surgically eligible BCCs. Moreover, "prevention of BCC" refers to preventing development of new BCC and/or n-SEBs in the entire body. In other embodiment, the term "prevention" refers to preventing development of new BCC and/or n-SEBs in the entire body wherein the subject (i) has or must have at least 6 facial BCC lesions at baseline, before treatment; or (ii) the subject must has or must have a genetic mutation PTCH; or (iii) the subject has or must have at least 6 BCC lesions at baseline, before treatment and a genetic mutation PTCH. In other embodiment, the term "prevention" refers to preventing development of new BCC and/or n-SEBs on the face wherein the subject (i) has or must have at least 6 facial BCC lesions at baseline, before treatment; or (ii) the subject has or must have a genetic mutation PTCH; or (iii) the subject has or must have at least 6 facial BCC lesions at baseline, before treatment and a genetic mutation PTCH. In another embodiment the subject has or must have a genetic mutation PTCH1 and suffers from Gorlin syndrome. In other embodiment, the term "prevention" refers to preventing development of new BCC and/or n-SEBs in the entire body wherein the subject must have Gorlin syndrome and genetic mutation PTCH1.

The terms "has" or "must have" are used herein interchangeably.

The term "Chronically" refers to more than 5 years, 10 years or longer, for lifetime.

The term "drug resistance" refers to a drug that is no longer effective.

The term "efficacy of the drug" refers to the effectiveness of the drug comprising prevention from reoccurrence of BCC and/or reduction in BCC lesion size/dimension over time.

In some embodiments, the treatment and/or prevention described herein refers to treatment and/or prevention of BCC, wherein the subject must have at least 6 BCC lesions at baseline, before treatment in any of the entire body. "Entire body" refers to any specific part of the body (i.e face, back, legs, hands, stomach etc.). Thus, the treatment comprises applying a composition comprising an effective amount of patidegib or a pharmaceutically acceptable salt thereof on the specific body part to be treated.

The term "facial BCC lesions" refers to BCC lesions on the face.

The term "BCC lesions" refers to BBC lesion in the entire body.

The term "clinically resolved BCC" or "resolved BCC" are used interchangeably and refer to no longer any visible evidence of a lesion consistent with BCC at the treated site as previously defined BBC lesion which is no longer BCC. In another embodiment, the term resolved BCC refers to BCC which disappeared completely.

In another embodiment, the term clinically resolved BCC refers to BCC which clinically disappeared completely.

The term "nSEB" refers to BCCs with a longest diameter of ≥5 mm that:

a. were not surgically eligible BCCs (SEBs) at baseline;
b. have grown by ≥2 mm in longest diameter from baseline; and
c. have been verified histologically.

Moreover, nSEB refers to a histologically verified new BCC that should be surgically removed because of possible functional facial/health impairment as determined by the Investigator.

The term "SEB" refers to surgically eligible BCCs with a longest diameter of ≥5 mm.

The term "resolved SEB lesions" refers to BCCs lesions which no longer requires a surgical removal treatment. In another embodiment the term "resolved SEB lesions" refers to BCCs lesions with a diameter <5 mm or the BCC lesions are completely disappeared.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present invention.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprise", "comprising", "includes", "including", "having" and their conjugates mean "including but not limited to".

The term "consisting of" means "including and limited to".

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Example 1—Gel Formulation

The Patidegib composition is a gel formulation presented in the following table.

Composition of Patidegib Topical Gel

| Component | Quality Standard | Concentration (wt %) Vehicle | 2% | 4% |
|---|---|---|---|---|
| patidegib | — | — | 2.0 [a] | 4.0 [a] |
| pH 7.5 borate buffer | — | 35.9 | 33.9 [b] | 31.9 [b] |
| dehydrated alcohol | USP, EP | 23.5 | 23.5 | 23.5 |
| DGME | NF, EP | 18.8 | 18.8 | 18.8 |
| propylene glycol | USP, EP | 18.8 | 18.8 | 18.8 |
| phenoxyethanol | NF, EP | 1.0 | 1.0 | 1.0 |
| HPC | NF, EP | 2.0 | 2.0 | 2.0 |

DGME, diethylene glycol monoethyl ether;
EP, European Pharmacopeia;
NF, National Formulary;
HPC, hydroxypropyl cellulose;
USP, United States Pharmacopeia;
—, not applicable
[a] free-base patidegib equivalent, excluding the bound hydrochloride salt, 2-propanol solvate, and water.
[b] reported concentration is inclusive of the bound hydrochloride salt, 2-propanol solvate, and water associated with the drug substance.

Example 2

A randomized, double-blind, stratified, vehicle-controlled study was done, measuring the efficacy and safety of Patidegib Topical Gel, 2%, applied topically twice daily to the face of adult participants with Gorlin syndrome. The Participants were required to apply the investigational product for 12 months. The primary endpoint is a comparison between the two treatment—Patidegib Topical Gel, 2%, versus Vehicle, resulted the of the number of new BCCs that develop over the 12 month period.

Experimental: Patidegib Topical Gel, 2%,

Participants will be randomized to receive Patidegib Topical Gel, 2%. The Patidegib Topical Gel, 2% will be dispensed to participants at each study visit and applied topically twice daily to the face.

Placebo Comparator: Patidegib Topical Gel, Vehicle

Participants will be randomized to receive Vehicle. The Patidegib Topical Gel, Vehicle will be dispensed to participants at each study visit and applied topically twice daily to the face.

Criteria for Participant

Inclusion Criteria:

1. The participant must be age at least 18 years of age at the Screening Visit.
2. The participant must provide written informed consent prior to any study procedures.
3. The participant must meet diagnostic criteria for the basal cell nevus (Gorlin) syndrome including PTCH1 gene mutation, or at least 6 histologically confirmed facial BCC lesions at Baseline and PTCH1 gene mutation.
4. The participant is willing to have blood collected to measure circulating drug levels.
5. The participant is willing to abstain from application of a non-study topical medication (prescription or over the counter) to facial skin for the duration of the trial except as prescribed by the Investigator. Moisturizers and emollients are allowed. Participant will be encouraged to use their preferred sunscreen with a sun protector factor (SPF) of at least 30 daily on all exposed skin sites.
6. If the participant is a woman of childbearing potential (WOCBP), she must be willing to use complete abstinence from sexual intercourse and/or she and her partner must be willing to use at least 2 highly-effective forms of birth control starting prior to Baseline, through the duration of the study, and for 12 months after last application of IP.
7. If the participant is a male with a female sex partner who is a WOCBP, the participant must be willing to use condoms, even after a vasectomy, starting prior to Baseline, through the duration of the study, and for at least 8 months after the last application of IP.
8. The participant is willing for all facial BCCs to be evaluated and treatment recommendations made only by the Investigator.
9. The participant is willing to forego treatment of facial BCCs with anything other than the study IP except when the Investigator believes that delay of treatment of a facial BCC potentially might compromise the health of the subject. During the trial the only allowed form of treatment is surgical. Non-facial BCCs may be removed at the discretion of the Investigator or Primary Skin Care Physician (PSCP).

Exclusion Criteria:

1. The subject has previously participated in a clinical trial evaluating patidegib topical gel.
2. The participant has used topical treatment to the face or systemic therapies that might interfere with the evaluation of the study IP. Among these are use of the following:
   a. 5-fluorouracil, imiquimod, diclofenac, or Ingenol mebutate (except as topical treatment to discrete non-facial BCCs) systemically or topically to the skin within the 2 months prior to the Screening Visit.
   b. Systemic chemotherapy within 1 year prior to the Screening Visit.
   c. Known inhibitors of the Hedgehog signaling pathway (such as vismodegib, sonidegib, itraconazole) topically or systemically within 3 months prior to the Screening Visit.
   d. Photodynamic therapy (PDT) except to localized non-facial, individual BCCs within 2 months prior to the Screening Visit.
3. The participant is known to have a hypersensitivity to any of the ingredients in the study medication formulation.
4. The participant is unable or unwilling to make a good faith effort to return to the study site for all study visits and tests.
5. The participant has uncontrolled systemic disease.
6. The participant has been treated for invasive cancer within the past 5 years excluding non-melanoma skin cancer, Stage I cervical cancer, ductal carcinoma in situ of the breast, or chronic lymphocytic leukemia (CLL) Stage 0.
7. The participant has current, recent (within five half-lives of the experimental drug or if half-life not known, within the past 6 months prior to the Screening Visit), or planned participation in an experimental drug study while enrolled in this study.
8. The participant is a WOCBP who is unwilling or unable to comply with pregnancy prevention measures.
9. The participant is pregnant or breastfeeding.
10. The participant has any condition or situation which, in the Investigator's opinion, may put the subject at significant risk, could confound the study results, or could interfere significantly with the subject's participation in the study. This may include a history of other skin conditions (such as severe facial eczema) or diseases, metabolic dysfunction, physical examination findings, or clinical laboratory findings giving reasonable suspicion of a disease or condition that contraindicates use of an investigational drug or that might affect interpretation of the results of the study or render the participant at high risk from treatment complications.

Results

Number of new BCCs excluding no longer suspicious BCCs, observed, in a subject with PTCH1 mutation as shown in FIG. 1 and table 1 as shown below:

TABLE 1

Analysis Variable: AVAL Analysis Value

| Description of Planned Arm | Analysis Visit (N) | N Obs* | N* | Mean | Std Error | Std Dev | Lower 95% CL for Mean | Upper 95% CL for Mean |
|---|---|---|---|---|---|---|---|---|
| Patidegib | 3 | 52 | 52 | 0.69 | 0.17 | 1.21 | 0.35 | 1.03 |
| | 6 | 37 | 37 | 1.59 | 0.34 | 2.05 | 0.91 | 2.28 |
| | 9 | 46 | 46 | 2.17 | 0.44 | 2.95 | 1.30 | 3.05 |
| | 12 | 44 | 44 | 2.61 | 0.39 | 2.59 | 1.83 | 3.40 |

TABLE 1-continued

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Vehicle | 3 | 58 | 58 | 0.95 | 0.18 | 1.39 | 0.58 | 1.31 |
| | 6 | 43 | 43 | 2.60 | 0.51 | 3.34 | 1.58 | 3.63 |
| | 9 | 49 | 49 | 3.22 | 0.55 | 3.88 | 2.11 | 4.34 |
| | 12 | 51 | 51 | 4.29 | 0.73 | 5.19 | 2.84 | 5.75 |

*N = number of patients.
*Nobs = Number of patients with clinical data.

As shown in Table 1 and FIG. 1, after 6 months of treatment with patidegib gel 2% the number of new BCCs excluding no longer suspicious BCCs is about 1.59, whereas to patients that were treated with vehicle is about 2.6. After 12 months of treatment with patidegib gel 2% the number of new BCCs excluding no longer suspicious BCCs is about 2.61, whereas to patients that were treated with vehicle is about 4.29. Therefore, administration of patidegib gel 2% prevents new BCC in a subject with PTCH1 mutation.

Figure 2:
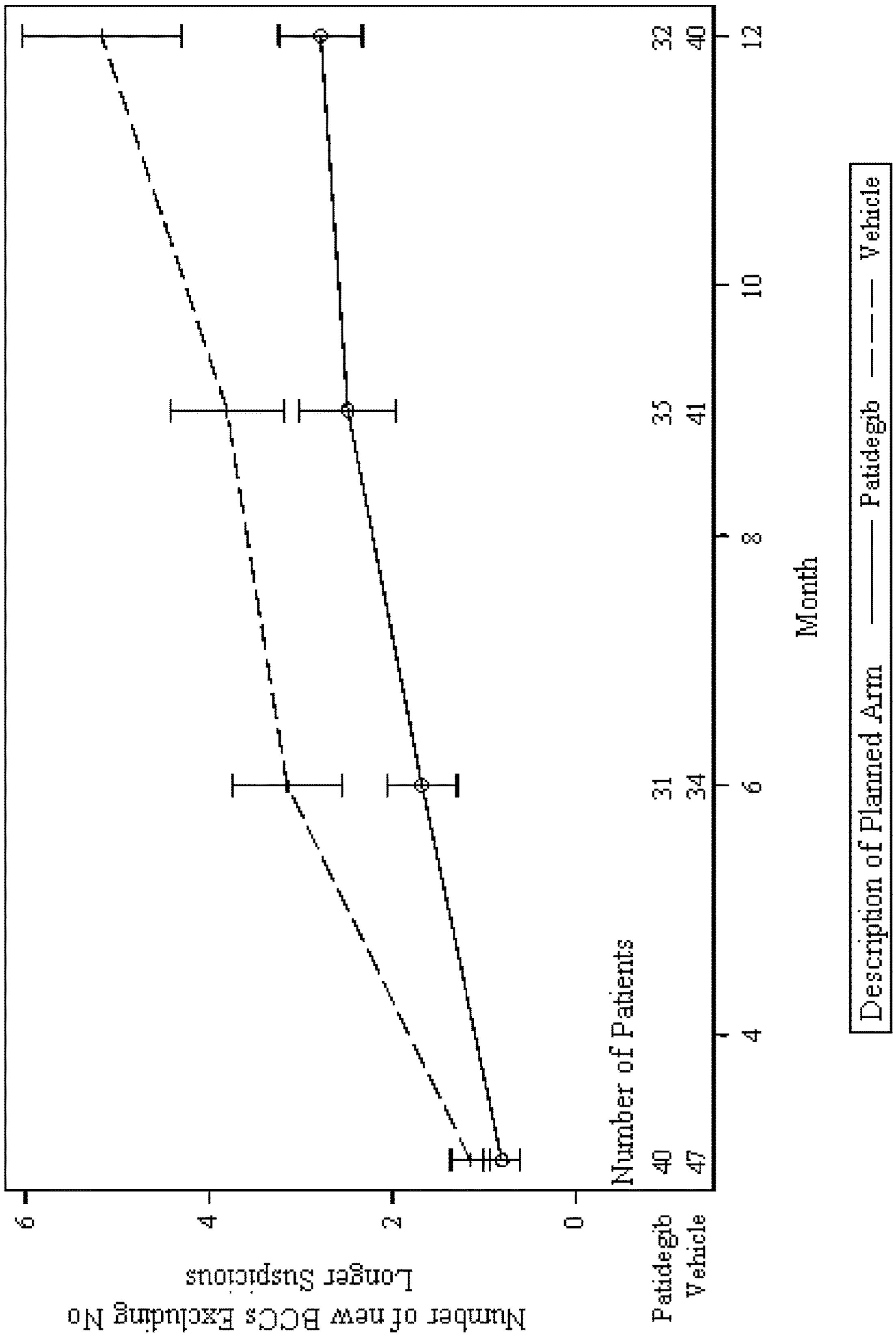
FIG. 2: Graphic illustration of number of new BCCs excluding no longer suspicious BCCs, observed, for subject suffering from PTCH1 mutation and has at least 6 facial BCC lesions at baseline. Based on the study described in Example 2.

Number of new BCCs excluding no longer suspicious BCCs, observed, in a subject with PTCH1 mutation and baseline total facial BCC lesions is at least 6, are shown in FIG. 2 and table 2 as shown below:

TABLE 2

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 40 | 40 | 0.80 | 0.20 | 1.29 | 0.39 | 1.21 |
| | 6 | 31 | 31 | 1.68 | 0.38 | 2.14 | 0.89 | 2.46 |
| | 9 | 35 | 35 | 2.49 | 0.53 | 3.12 | 1.41 | 3.56 |
| | 12 | 32 | 32 | 2.78 | 0.46 | 2.57 | 1.85 | 3.71 |
| Vehicle | 3 | 47 | 47 | 1.15 | 0.22 | 1.47 | 0.72 | 1.58 |
| | 6 | 34 | 34 | 3.15 | 0.60 | 3.51 | 1.92 | 4.37 |
| | 9 | 41 | 41 | 3.80 | 0.62 | 3.98 | 2.55 | 5.06 |
| | 12 | 40 | 40 | 5.18 | 0.87 | 5.47 | 3.42 | 6.93 |

*N = number of patients.
*Nobs = Number of patients with clinical data.

As shown in Table 2 and FIG. 2, after 6 months of treatment with patidegib gel 2% the number of new BCCs excluding no longer suspicious BCCs is about 1.68, whereas to patients that were treated with vehicle is about 3.15. After 12 months of treatment with patidegib gel 2% the number of new BCCs excluding no longer suspicious BCCs is about 2.78, whereas to patients that were treated with vehicle is about 5.18. Therefore, administration of patidegib gel 2% prevents new BCC in a subject with PTCH1 mutation and baseline total facial BCC lesions is at least 6.

Figure 3:
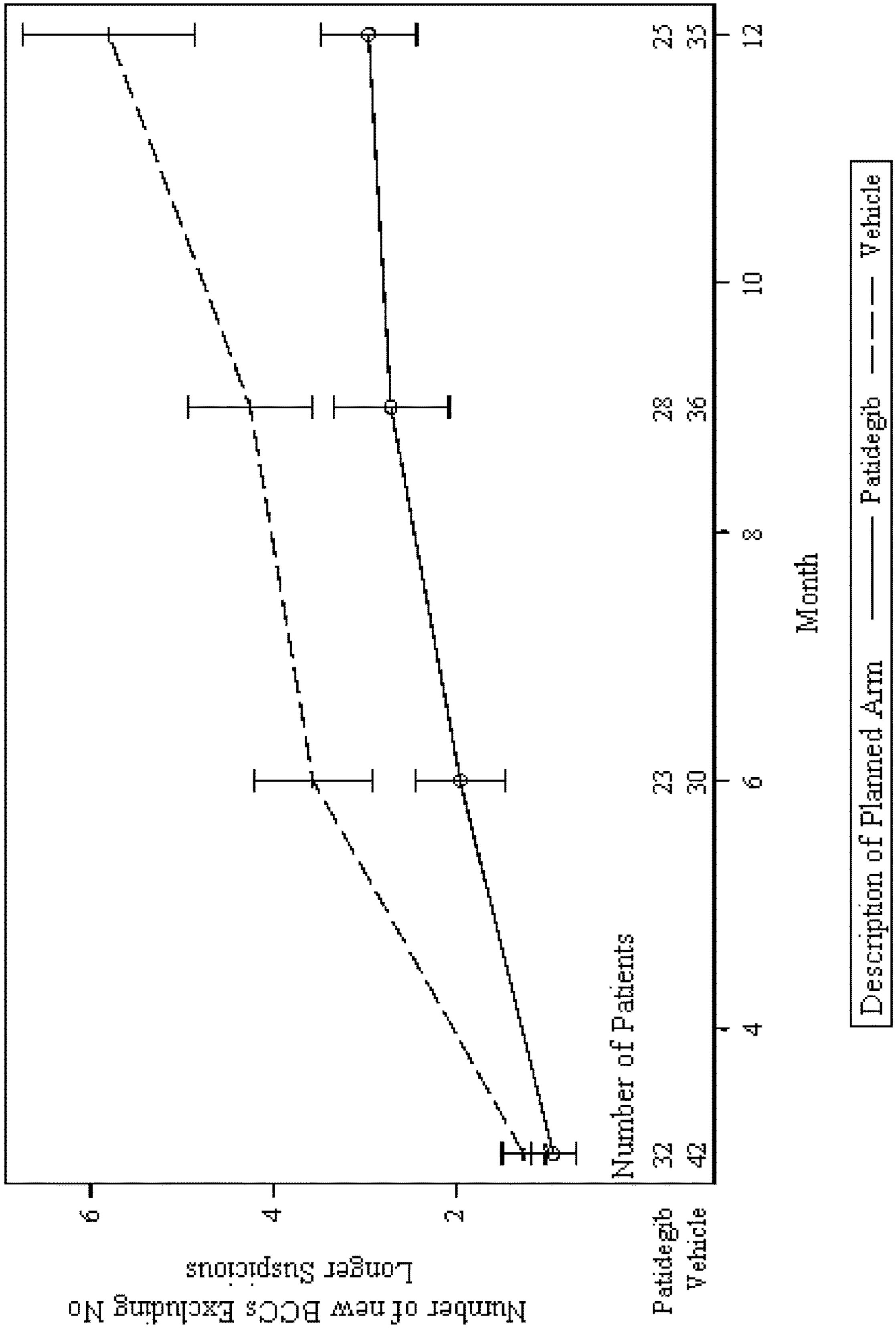
FIG. 3: Graphic illustration of number of new BCCs excluding no longer suspicious BCCs, observed, for subject suffering from PTCH1 mutation and has at least 8 facial BCC lesions at baseline. Based on the study described in Example 2.

Number of new BCCs excluding no longer suspicious BCCs, observed, in a subject with PTCH1 mutation and baseline total facial BCC lesions is at least 8, are shown in FIG. 3 and table 3 as shown below:

TABLE 3

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 32 | 32 | 0.94 | 0.25 | 1.39 | 0.44 | 1.44 |
| | 6 | 23 | 23 | 1.96 | 0.49 | 2.34 | 0.94 | 2.97 |
| | 9 | 28 | 28 | 2.71 | 0.63 | 3.33 | 1.42 | 4.01 |
| | 12 | 25 | 25 | 2.96 | 0.52 | 2.62 | 1.88 | 4.04 |

TABLE 3-continued

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Vehicle | 3 | 42 | 42 | 1.26 | 0.23 | 1.52 | 0.79 | 1.73 |
| | 6 | 30 | 30 | 3.57 | 0.64 | 3.53 | 2.25 | 4.88 |
| | 9 | 36 | 36 | 4.25 | 0.67 | 4.05 | 2.88 | 5.62 |
| | 12 | 35 | 35 | 5.80 | 0.94 | 5.57 | 3.89 | 7.71 |

*N = number of patients.
*Nobs = Number of patients with clinical data.

As shown in Table 3 and FIG. 3, after 6 months of treatment with patidegib gel 2% the number of new BCCs excluding no longer suspicious BCCs is about 1.96, whereas to patients that were treated with vehicle is about 3.57. After 12 months of treatment with patidegib gel 2% the number of new BCCs excluding no longer suspicious BCCs is about 2.96, whereas to patients that were treated with vehicle is about 5.80. Therefore, administration of patidegib gel 2% prevents new BCC in a subject with PTCH1 mutation and baseline total facial BCC lesions is at least 8.

Figure 4:
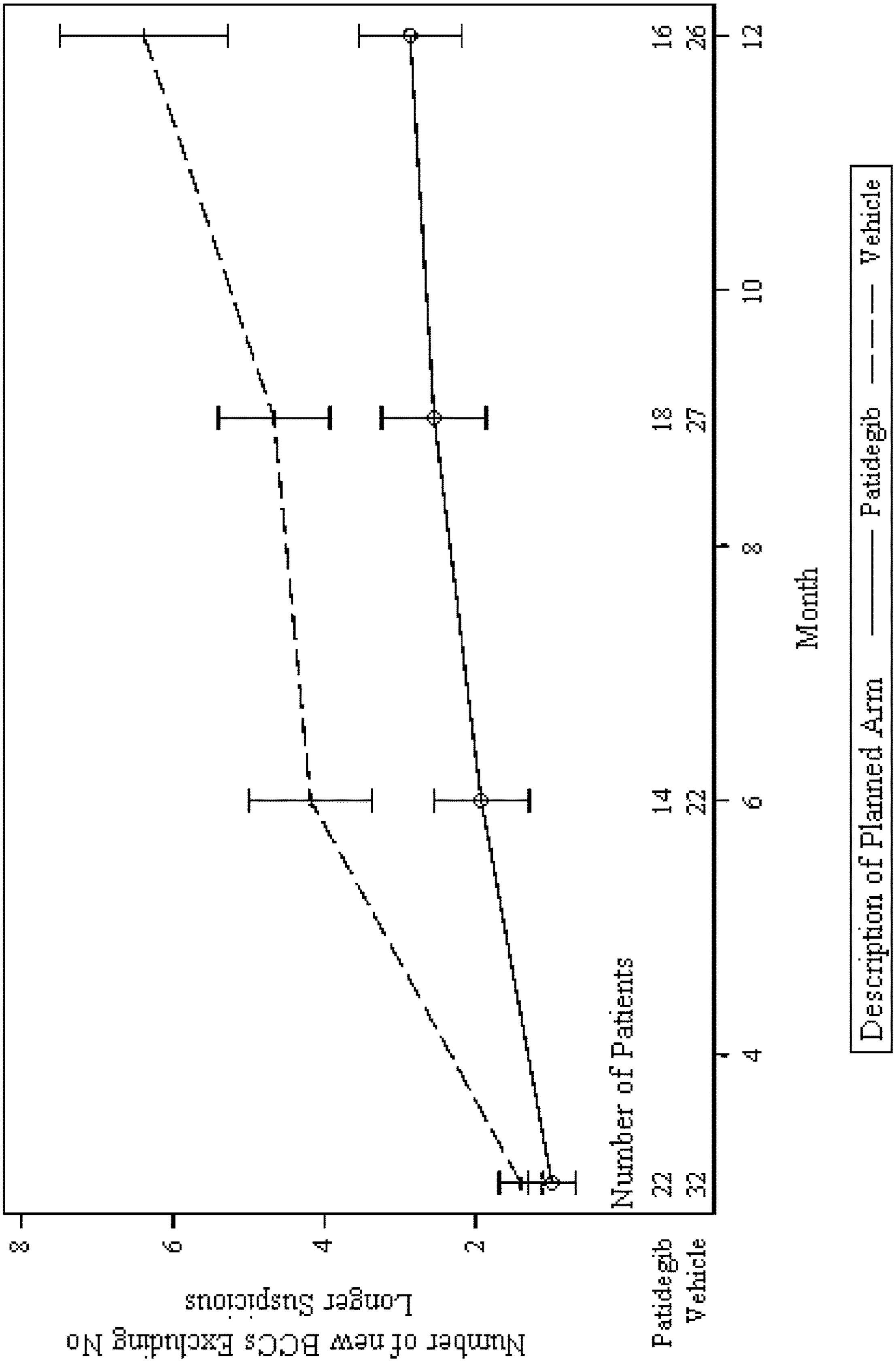
FIG. 4: Graphic illustration of number of new BCCs excluding no longer suspicious BCCs, observed, for subject suffering from PTCH1 mutation and has at least 10 facial BCC lesions at baseline. Based on the study described in Example 2.

Number of new BCCs excluding no longer suspicious BCCs, observed, in a subject with PTCH1 mutation and baseline total facial BCC lesions is at least 10, are shown in FIG. 4 and table 4 as shown below:

TABLE 4

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 22 | 22 | 1.00 | 0.31 | 1.45 | 0.36 | 1.64 |
| | 6 | 14 | 14 | 1.93 | 0.63 | 2.37 | 0.56 | 3.30 |
| | 9 | 18 | 18 | 2.56 | 0.69 | 2.94 | 1.10 | 4.02 |
| | 12 | 16 | 16 | 2.88 | 0.68 | 2.73 | 1.42 | 4.33 |
| Vehicle | 3 | 32 | 32 | 1.41 | 0.28 | 1.60 | 0.83 | 1.98 |
| | 6 | 22 | 22 | 4.18 | 0.81 | 3.80 | 2.50 | 5.87 |
| | 9 | 27 | 27 | 4.67 | 0.74 | 3.84 | 3.15 | 6.19 |
| | 12 | 26 | 26 | 6.38 | 1.10 | 5.60 | 4.12 | 8.65 |

*N = number of patients.
*Nobs = Number of patients with clinical data.

As shown in Table 4 and FIG. 4, after 6 months of treatment with patidegib gel 2% the number of new BCCs excluding no longer suspicious BCCs is about 1.93, whereas to patients that were treated with vehicle is about 4.18. After 12 months of treatment with patidegib gel 2% the number of new BCCs excluding no longer suspicious BCCs is about 2.88, whereas to patients that were treated with vehicle is about 6.38. Therefore, administration of patidegib gel 2% prevents new BCC in a subject with PTCH1 mutation and baseline total facial BCC lesions is at least 10.

Figure 5:
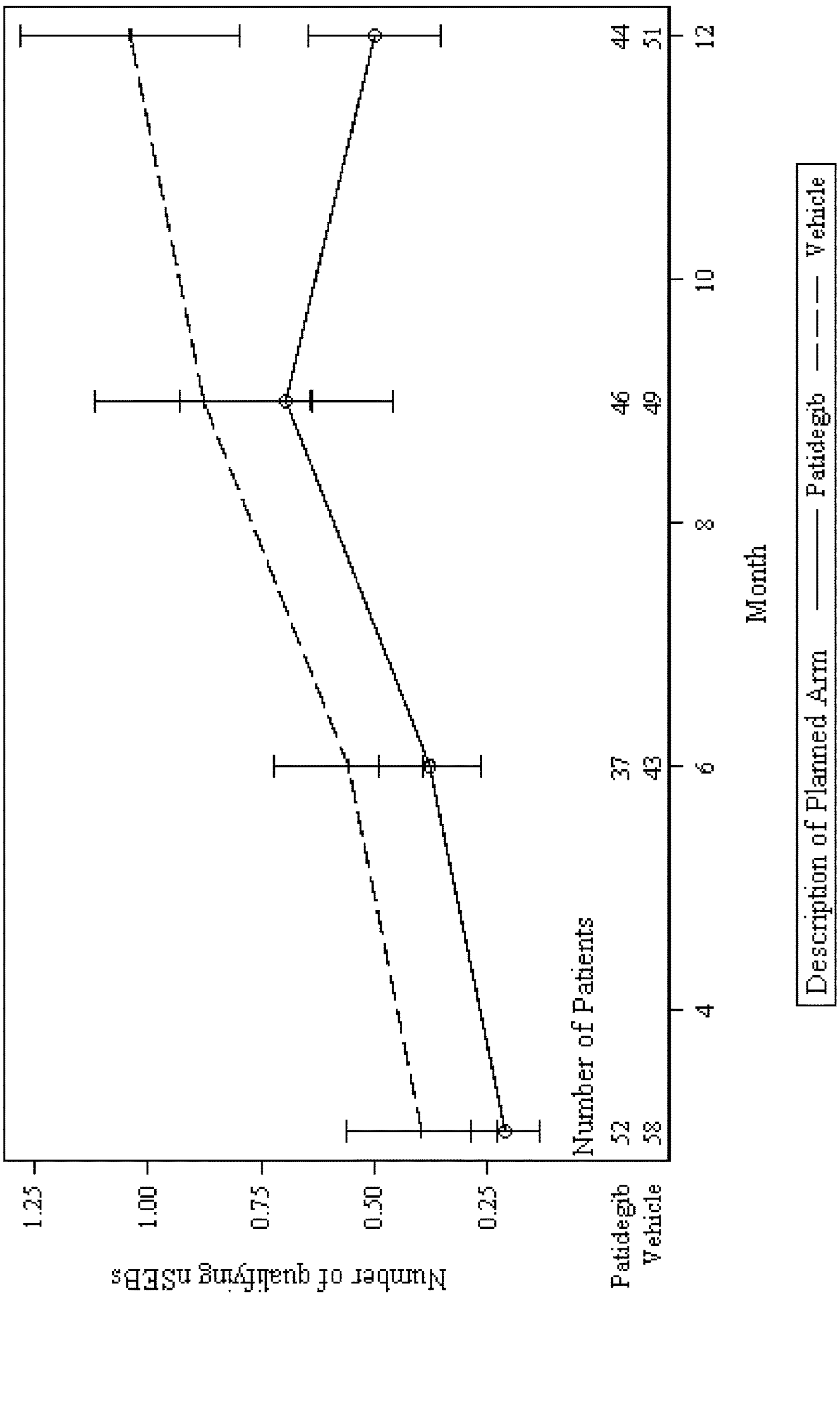
FIG. 5: Graphic illustration of number of qualifying new surgically eligible BCCs (nSEBs), observed, for subject suffering from PTCH1 mutation. Based on the study described in Example 2.

Number of qualifying nSEBs, observed, in a subject with PTCH1 mutation, are shown in FIG. 5 and table 5 as shown below:

TABLE 5

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 52 | 52 | 0.21 | 0.07 | 0.54 | 0.06 | 0.36 |
| | 6 | 37 | 37 | 0.38 | 0.11 | 0.68 | 0.15 | 0.61 |
| | 9 | 46 | 46 | 0.70 | 0.23 | 1.59 | 0.22 | 1.17 |
| | 12 | 44 | 44 | 0.50 | 0.15 | 0.98 | 0.20 | 0.80 |

TABLE 5-continued

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Vehicle | 3 | 58 | 58 | 0.40 | 0.17 | 1.27 | 0.06 | 0.73 |
| | 6 | 43 | 43 | 0.56 | 0.16 | 1.08 | 0.23 | 0.89 |
| | 9 | 49 | 49 | 0.88 | 0.24 | 1.67 | 0.40 | 1.36 |
| | 12 | 51 | 51 | 1.04 | 0.24 | 1.73 | 0.55 | 1.53 |

*N = number of patients.
*Nobs = Number of patients with clinical data.

As shown in Table 5 and FIG. 5, after 6 months of treatment with patidegib gel 2% the number of qualifying nSEBs is about 0.38, whereas to patients that were treated with vehicle is about 0.56. After 12 months of treatment with patidegib gel 2% the number of qualifying nSEBs is about 0.5, whereas to patients that were treated with vehicle is about 1.04. Therefore, administration of patidegib gel 2% lowers the number of qualifying nSEBs in a subject with PTCH1 mutation.

Figure 6:
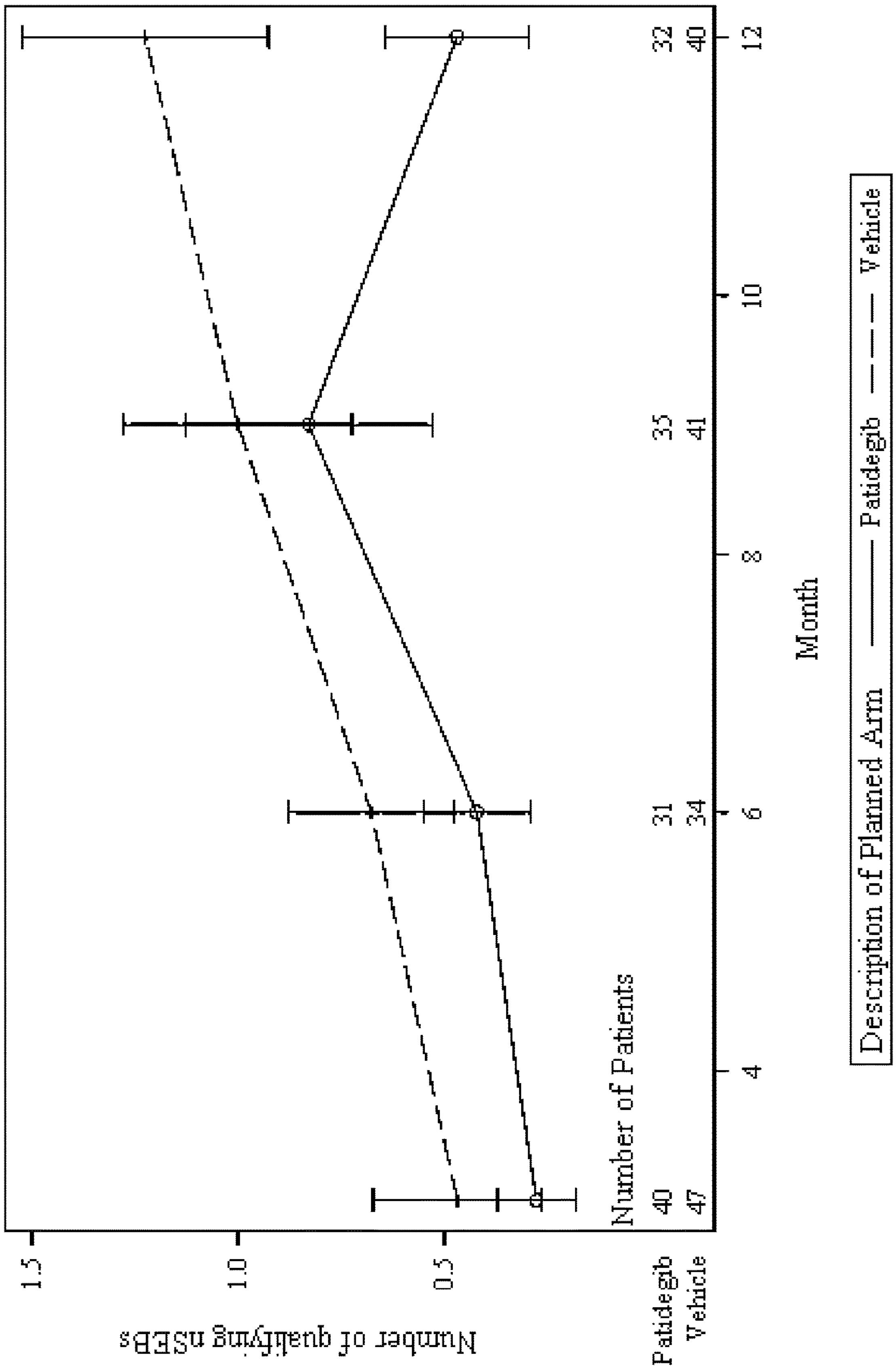
FIG. 6: Graphic illustration of number of qualifying nSEBs, observed, for subject suffering from PTCH1 mutation and has at least 6 facial BCC lesions at baseline. Based on the study described in Example 2.

Number of qualifying nSEBs, observed, in a subject with PTCH1 mutation and baseline total BCC facial lesions is at least 6, are shown in FIG. 6 and table 6 as shown below:

TABLE 6

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 40 | 40 | 0.28 | 0.09 | 0.60 | 0.08 | 0.47 |
| | 6 | 31 | 31 | 0.42 | 0.13 | 0.72 | 0.16 | 0.68 |
| | 9 | 35 | 35 | 0.83 | 0.30 | 1.77 | 0.22 | 1.44 |
| | 12 | 32 | 32 | 0.47 | 0.17 | 0.98 | 0.11 | 0.82 |
| Vehicle | 3 | 47 | 47 | 0.47 | 0.20 | 1.40 | 0.06 | 0.88 |
| | 6 | 34 | 34 | 0.68 | 0.20 | 1.17 | 0.27 | 1.09 |
| | 9 | 41 | 41 | 1.00 | 0.28 | 1.77 | 0.44 | 1.56 |
| | 12 | 40 | 40 | 1.23 | 0.30 | 1.89 | 0.62 | 1.83 |

*N = number of patients.
*Nobs = Number of patients with clinical data.

As shown in Table 6 and FIG. 6, after 6 months of treatment with patidegib gel 2% the number of qualifying nSEBs is about 0.42, whereas to patients that were treated with vehicle is about 0.68. After 12 months of treatment with patidegib gel 2% the number of qualifying nSEBs is about 0.47, whereas to patients that were treated with vehicle is about 1.23. Therefore, administration of patidegib gel 2% lowers the number of qualifying nSEBs in a subject with PTCH1 mutation and baseline total facial BCC lesions is at least 6.

Figure 7:
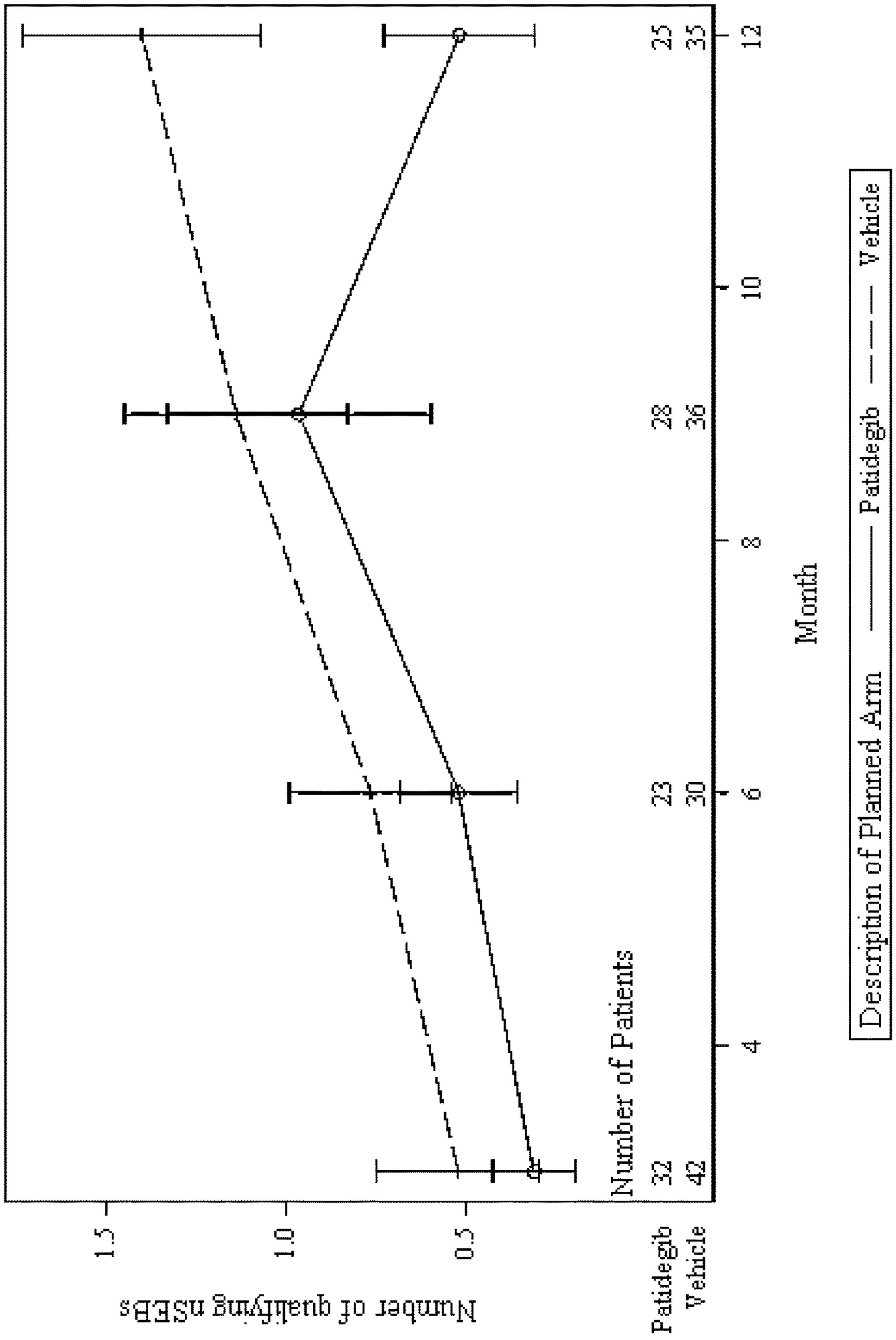
FIG. 7: Graphic illustration of number of qualifying nSEBs, observed, for subject suffering from PTCH1 mutation and has at least 8 facial BCC lesions at baseline. Based on the study described in Example 2.

Number of qualifying nSEBs, observed, in a subject with PTCH1 mutation and baseline total facial BCC lesions is at least 8, are shown in FIG. 7 and table 7 as shown below:

TABLE 7

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 32 | 32 | 0.31 | 0.11 | 0.64 | 0.08 | 0.54 |
| | 6 | 23 | 23 | 0.52 | 0.16 | 0.79 | 0.18 | 0.86 |
| | 9 | 28 | 28 | 0.96 | 0.37 | 1.93 | 0.21 | 1.71 |
| | 12 | 25 | 25 | 0.52 | 0.21 | 1.05 | 0.09 | 0.95 |

TABLE 7-continued

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Vehicle | 3 | 42 | 42 | 0.52 | 0.23 | 1.47 | 0.07 | 0.98 |
| | 6 | 30 | 30 | 0.77 | 0.22 | 1.22 | 0.31 | 1.22 |
| | 9 | 36 | 36 | 1.14 | 0.31 | 1.85 | 0.51 | 1.77 |
| | 12 | 35 | 35 | 1.40 | 0.33 | 1.96 | 0.73 | 2.07 |

*N = number of patients.
*Nobs = Number of patients with clinical data.

As shown in Table 7 and FIG. 7, after 6 months of treatment with patidegib gel 2% the number of qualifying nSEBs is about 0.52, whereas to patients that were treated with vehicle is about 0.77. After 12 months of treatment with patidegib gel 2% the number of qualifying nSEBs is about 0.52, whereas to patients that were treated with vehicle is about 1.40. Therefore, administration of patidegib gel 2% lowers the number of qualifying nSEBs in a subject with PTCH1 mutation and baseline total facial BCC lesions is at least 8.

Figure 8:
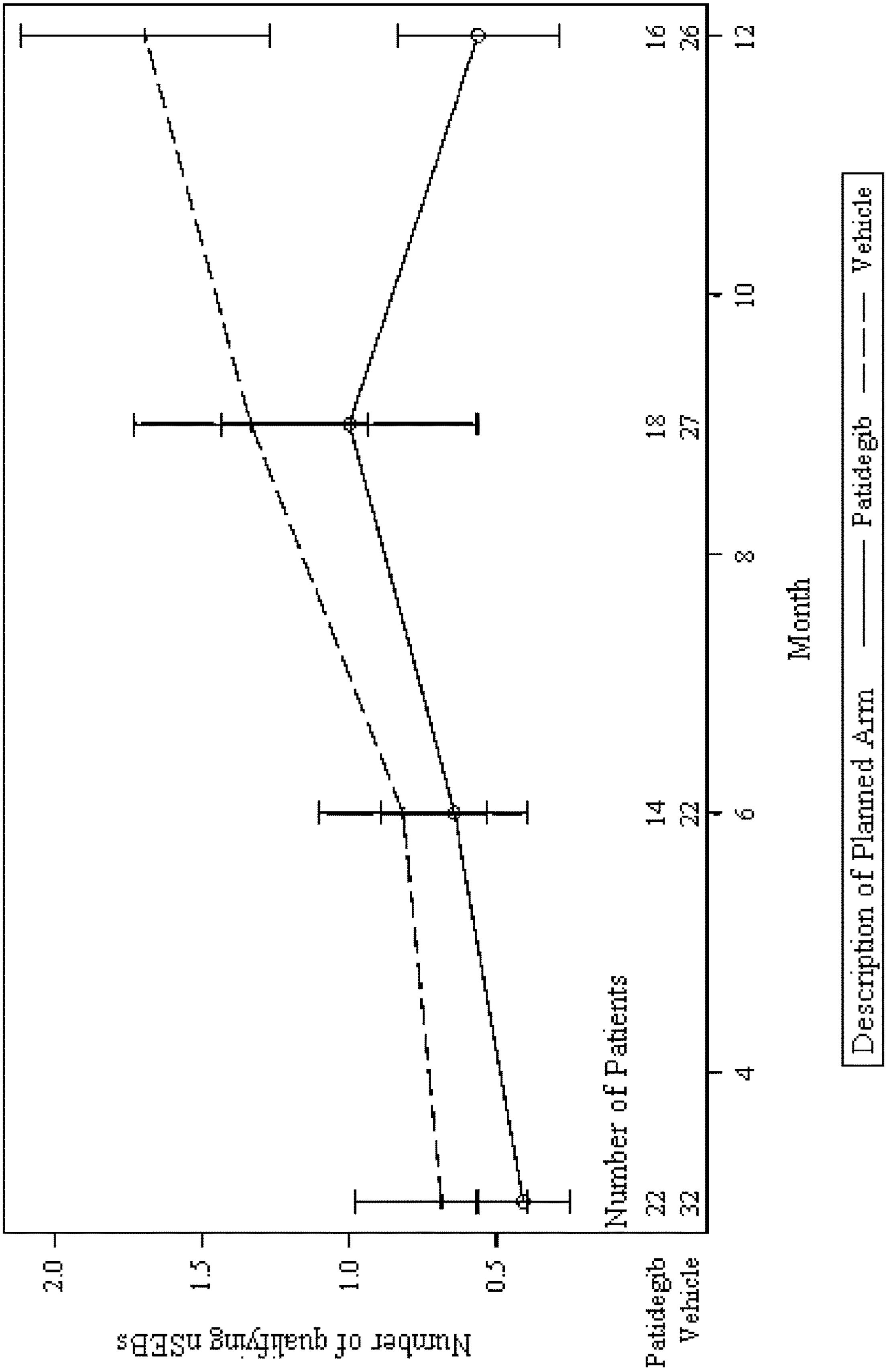
FIG. 8: Graphic illustration of number of qualifying nSEBs, observed, for subject suffering from PTCH1 mutation and has at least 10 facial BCC lesions at baseline. Based on the study described in Example 2.

Number of qualifying nSEBs, observed, in a subject with PTCH1 mutation and baseline total facial BCC lesions are at least 10, are shown in FIG. 8 and table 8 as shown below:

TABLE 8

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 22 | 22 | 0.41 | 0.16 | 0.73 | 0.08 | 0.73 |
| | 6 | 14 | 14 | 0.64 | 0.25 | 0.93 | 0.11 | 1.18 |
| | 9 | 18 | 18 | 1.00 | 0.44 | 1.85 | 0.08 | 1.92 |
| | 12 | 16 | 16 | 0.56 | 0.27 | 1.09 | −0.02 | 1.15 |
| Vehicle | 3 | 32 | 32 | 0.69 | 0.29 | 1.65 | 0.09 | 1.28 |
| | 6 | 22 | 22 | 0.82 | 0.28 | 1.33 | 0.23 | 1.41 |
| | 9 | 27 | 27 | 1.33 | 0.40 | 2.06 | 0.52 | 2.15 |
| | 12 | 26 | 26 | 1.69 | 0.42 | 2.15 | 0.82 | 2.56 |

*N = number of patients.
*Nobs = Number of patients with clinical data.

As shown in Table 8 and FIG. 8, after 6 months of treatment with patidegib gel 2% the number of qualifying nSEBs is about 0.64, whereas to patients that were treated with vehicle is about 0.82. After 12 months of treatment with patidegib gel 2% the number of qualifying nSEBs is about 0.56, whereas to patients that were treated with vehicle is about 1.69. Therefore, administration of patidegib gel 2% lowers the number of qualifying nSEBs in a subject with PTCH1 mutation and baseline total facial BCC lesions is at least 10.

Figure 9:
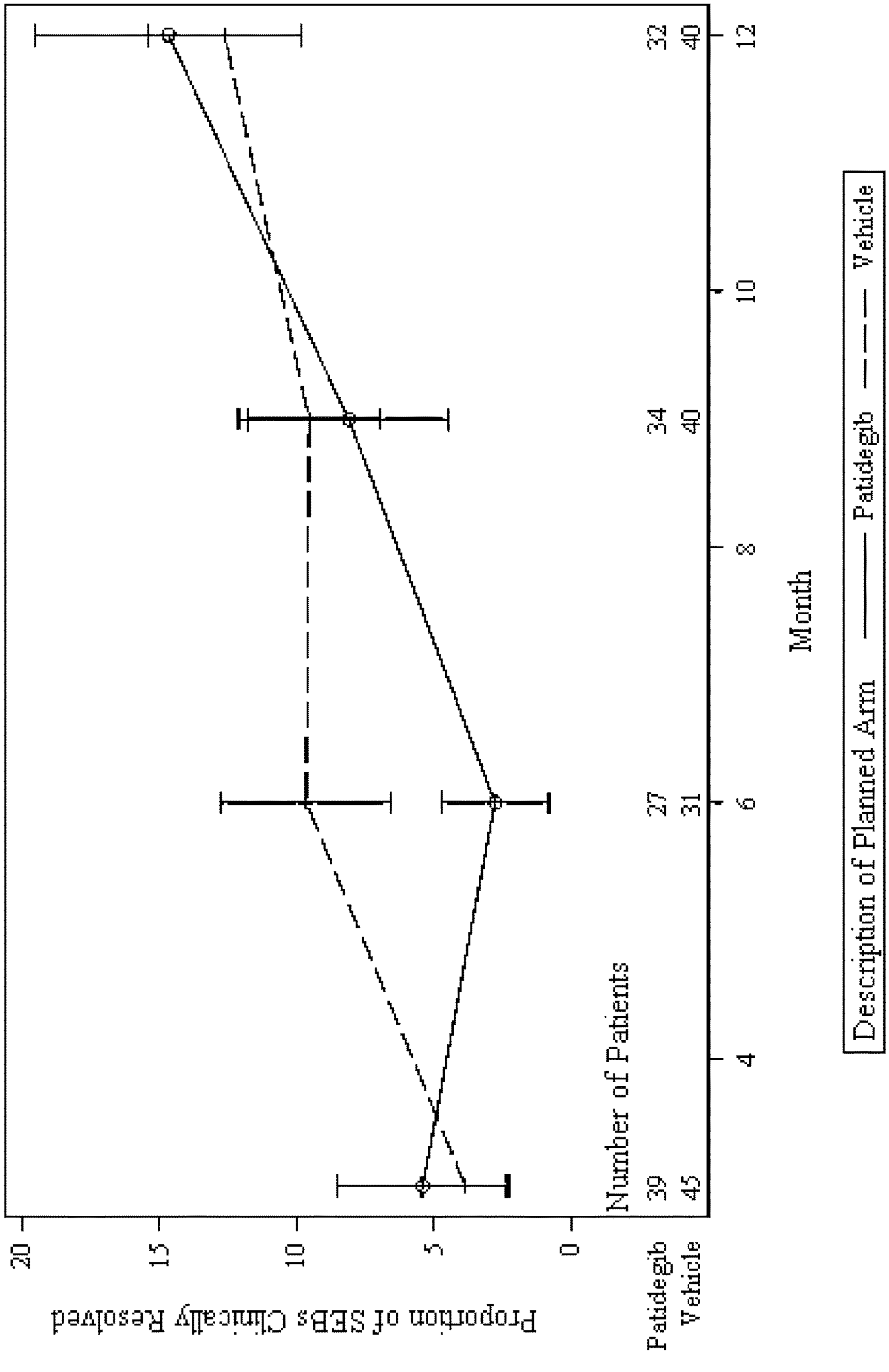
FIG. 9: Graphic illustration of proportion of SEBs resolved, observed, in a subject with PTCH1 mutation. Based on the study described in Example 2.

Proportion of SEBs clinically resolved, observed, in a subject with PTCH1 mutation, are shown in FIG. 9 and table 9 as shown below:

TABLE 9

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 39 | 39 | 5.42 | 3.07 | 19.15 | −0.79 | 11.63 |
| | 6 | 27 | 27 | 2.76 | 1.97 | 10.22 | −1.28 | 6.81 |
| | 9 | 34 | 34 | 8.11 | 3.66 | 21.35 | 0.66 | 15.57 |
| | 12 | 32 | 32 | 14.68 | 4.86 | 27.51 | 4.76 | 24.60 |

TABLE 9-continued

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Vehicle | 3 | 45 | 45 | 3.85 | 1.61 | 10.77 | 0.62 | 7.09 |
| | 6 | 31 | 31 | 9.65 | 3.10 | 17.27 | 3.31 | 15.99 |
| | 9 | 40 | 40 | 9.55 | 2.57 | 16.23 | 4.36 | 14.74 |
| | 12 | 40 | 40 | 12.62 | 2.78 | 17.58 | 7.00 | 18.24 |

*N = number of patients.
*Nobs = Number of patients with clinical data.

As shown in Table 9 and FIG. 9, after 9 months of treatment with patidegib gel 2% the proportion of SEBs clinically resolved is about 8.11, whereas to patients that were treated with vehicle is about 9.55. After 12 months of treatment with patidegib gel 2% the proportion of SEBs clinically resolved is about 14.68, whereas to patients that were treated with vehicle is about 12.62. Therefore, administration of patidegib gel 2% elevates the proportion of SEBs clinically resolved in a subject with PTCH1 mutation in comparison to the administration of a vehicle.

Figure 10:
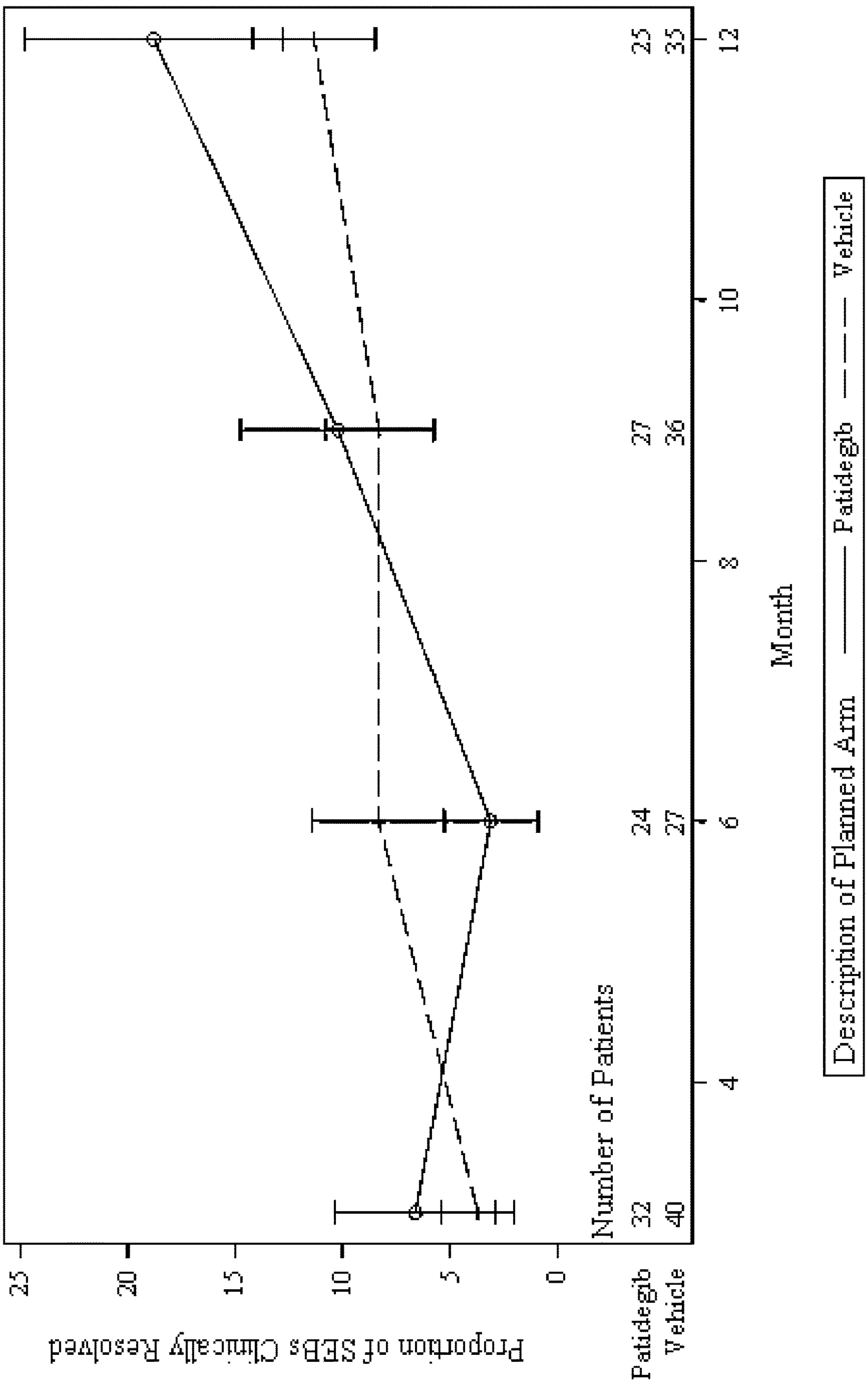
FIG. 10: Graphic illustration of proportion of SEBs resolved, observed, in a subject with PTCH1 mutation and has at least 6 facial BCC lesions at baseline. Based on the study described in Example 2.

Proportion of SEBs clinically resolved, observed, in a subject with PTCH1 mutation and baseline total facial BCC lesions are at least 6, are shown in FIG. 10 and table 10 as shown below:

TABLE 10

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 32 | 32 | 6.61 | 3.72 | 21.02 | −0.97 | 14.18 |
| | 6 | 24 | 24 | 3.11 | 2.21 | 10.81 | −1.46 | 7.68 |
| | 9 | 27 | 27 | 10.22 | 4.54 | 23.59 | 0.89 | 19.55 |
| | 12 | 25 | 25 | 18.79 | 5.99 | 29.95 | 6.43 | 31.15 |
| Vehicle | 3 | 40 | 40 | 3.71 | 1.72 | 10.86 | 0.24 | 7.18 |
| | 6 | 27 | 27 | 8.30 | 3.12 | 16.24 | 1.88 | 14.73 |
| | 9 | 36 | 36 | 8.30 | 2.49 | 14.96 | 3.23 | 13.36 |
| | 12 | 35 | 35 | 11.33 | 2.86 | 16.89 | 5.52 | 17.13 |

*N = number of patients.
*Nobs = Number of patients with clinical data.

As shown in Table 10 and FIG. 10, after 9 months of treatment with patidegib gel 2% the proportion of SEBs clinically resolved is about 10.22, whereas to patients that were treated with vehicle is about 8.30. After 12 months of treatment with patidegib gel 2% the proportion of SEBs clinically resolved is about 18.79, whereas to patients that were treated with vehicle is about 11.33. Therefore, administration of patidegib gel 2% elevates the proportion of SEBs clinically resolved in a subject with PTCH1 mutation and baseline total facial BCC lesions is at least 6 in comparison to the administration of a vehicle.

Figure 11:
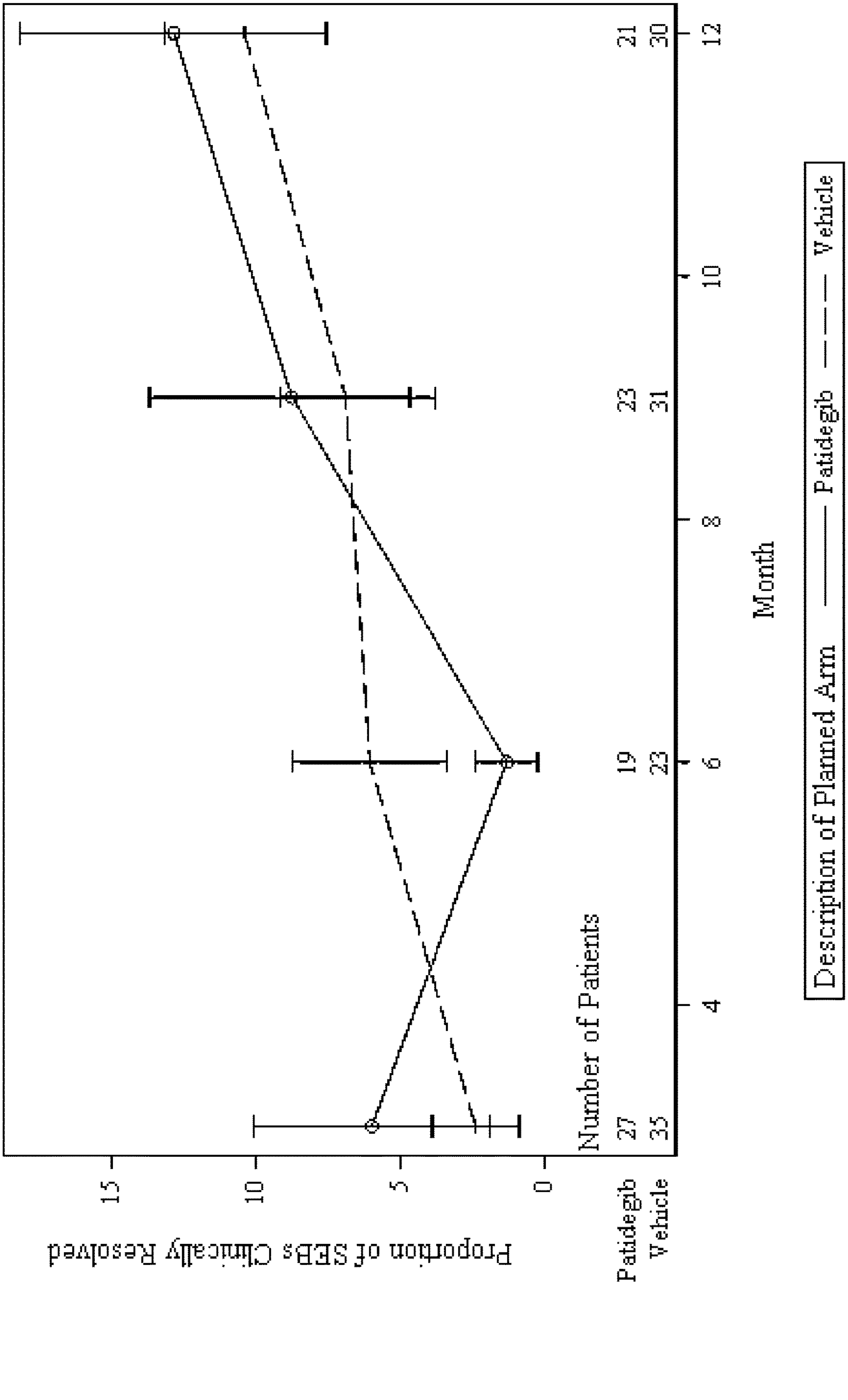
FIG. 11: Graphic illustration of proportion of SEBs resolved, observed, in a subject with PTCH1 mutation and has at least 8 facial BCC lesions at baseline. Based on the study described in Example 2.

Proportion of SEBs clinically resolved, observed, in a subject with PTCH1 mutation and baseline total facial BCC lesions are at least 8, are shown in FIG. 11 and table 11 as shown below:

TABLE 11

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 27 | 27 | 5.98 | 4.07 | 21.14 | −2.39 | 14.34 |
| | 6 | 19 | 19 | 1.30 | 1.07 | 4.65 | −0.95 | 3.54 |
| | 9 | 23 | 23 | 8.73 | 4.95 | 23.75 | −1.53 | 19.00 |
| | 12 | 21 | 21 | 12.84 | 5.32 | 24.38 | 1.75 | 23.94 |

TABLE 11-continued

Analysis Variable: AVAL Analysis Value

| Description of Planned Arm | Analysis Visit (N) | N Obs* | N* | Mean | Std Error | Std Dev | Lower 95% CL for Mean | Upper 95% CL for Mean |
|---|---|---|---|---|---|---|---|---|
| Vehicle | 3 | 35 | 35 | 2.38 | 1.51 | 8.95 | −0.69 | 5.46 |
| | 6 | 23 | 23 | 6.05 | 2.68 | 12.88 | 0.48 | 11.62 |
| | 9 | 31 | 31 | 6.89 | 2.23 | 12.41 | 2.34 | 11.44 |
| | 12 | 30 | 30 | 10.38 | 2.78 | 15.24 | 4.69 | 16.07 |

*N = number of patients.
*Nobs = Number of patients with clinical data.

As shown in Table 11 and FIG. 11, after 9 months of treatment with patidegib gel 2% the proportion of SEBs clinically resolved is about 8.73, whereas to patients that were treated with vehicle is about 6.89. After 12 months of treatment with patidegib gel 2% the proportion of SEBs clinically resolved is about 12.84, whereas to patients that were treated with vehicle is about 10.38. Therefore, administration of patidegib gel 2% elevates the proportion of SEBs clinically resolved in a subject with PTCH1 mutation and baseline total facial BCC lesions is at least 8 in comparison to the administration of a vehicle.

Figure 12:
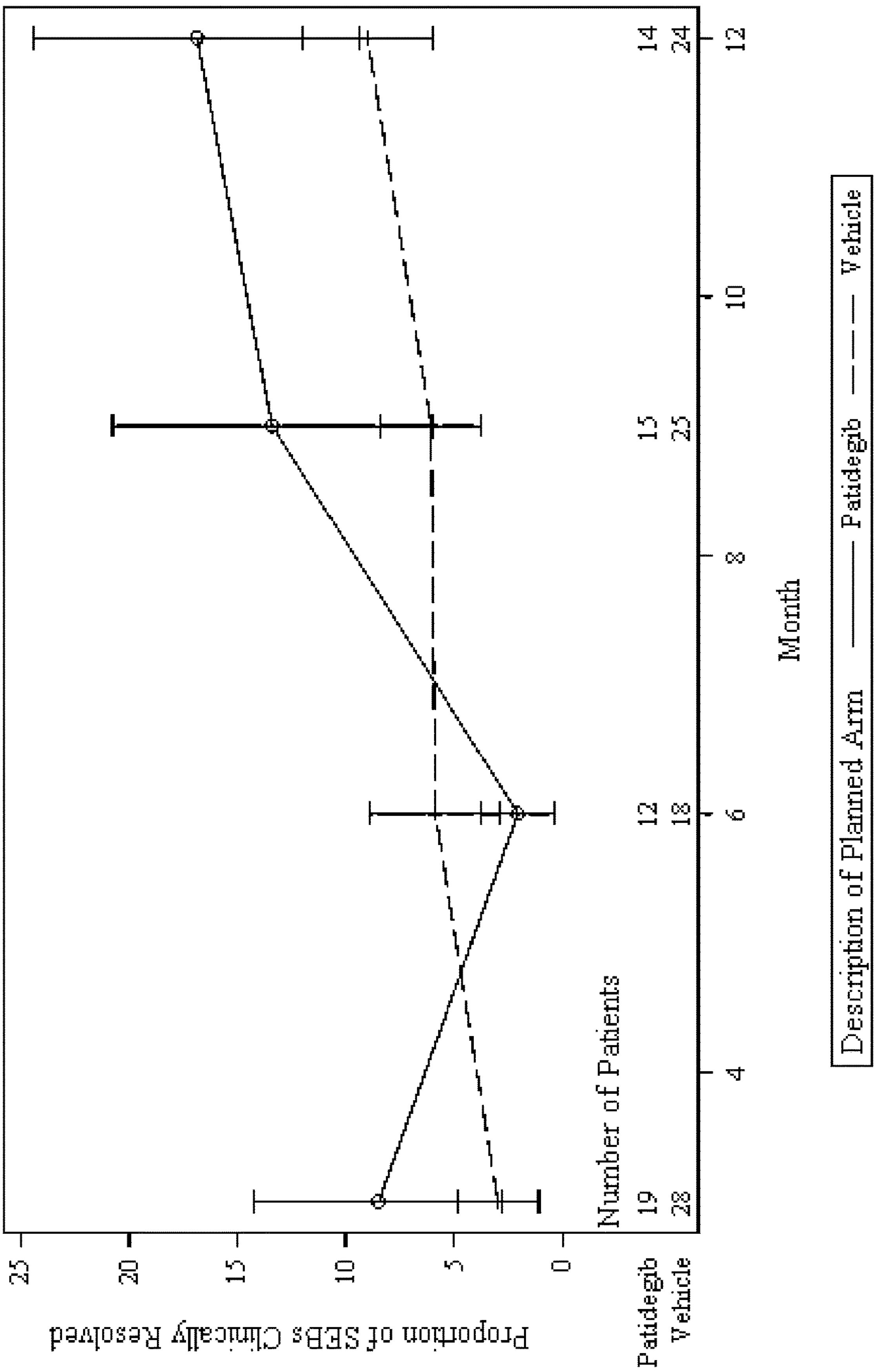
FIG. 12: Graphic illustration of proportion of SEBs resolved, observed, in a subject with PTCH1 mutation and has at least 10 facial BCC lesions at baseline. Based on the study described in Example 2.

Proportion of SEBs clinically resolved, observed, in a subject with PTCH1 mutation and baseline total facial BCC lesions are at least 10, are shown in FIG. 12 and table 12 as shown below:

TABLE 12

Analysis Variable: AVAL Analysis Value

| Description of Planned Arm | Analysis Visit (N) | N Obs | N | Mean | Std Error | Std Dev | Lower 95% CL for Mean | Upper 95% CL for Mean |
|---|---|---|---|---|---|---|---|---|
| Patidegib | 3 | 19 | 19 | 8.50 | 5.73 | 24.96 | −3.54 | 20.53 |
| | 6 | 12 | 12 | 2.05 | 1.68 | 5.81 | −1.64 | 5.74 |
| | 9 | 15 | 15 | 13.39 | 7.39 | 28.62 | −2.46 | 29.24 |
| | 12 | 14 | 14 | 16.89 | 7.51 | 28.08 | 0.67 | 33.10 |
| Vehicle | 3 | 28 | 28 | 2.98 | 1.88 | 9.95 | −0.88 | 6.84 |
| | 6 | 18 | 18 | 5.88 | 3.00 | 12.73 | −0.45 | 12.21 |
| | 9 | 25 | 25 | 6.07 | 2.32 | 11.62 | 1.27 | 10.87 |
| | 12 | 24 | 24 | 9.01 | 3.00 | 14.72 | 2.80 | 15.22 |

*N = number of patients.
*Nobs = Number of patients with clinical data.

As shown in Table 12 and FIG. 12, after 9 months of treatment with patidegib gel 2% the proportion of SEBs clinically resolved is about 13.39, whereas to patients that were treated with vehicle is about 6.07. After 12 months of treatment with patidegib gel 2% the proportion of SEBs clinically resolved is about 16.89, whereas to patients that were treated with vehicle is about 9.01. Therefore, administration of patidegib gel 2% elevates the proportion of SEBs clinically resolved in a subject with PTCH1 mutation and baseline total facial BCC lesions is at least 8 in comparison to the administration of a vehicle.

Number of new BCC per subject by month 12, observed, in a subject with PTCH1 mutation, are shown in table 13 as shown below:

TABLE 13

| | Patidegib | Vehicle |
|---|---|---|
| Number of subjects at Baseline | 44 | 50 |
| Number of BCCs at Baseline-Mean (SD) | 13.02 (11.15) | 15.24 (10.45) |
| Median | 10.0 | 11.0 |
| Min, Max | 2, 66 | 2, 50 |
| Q1, Q3 | 7.0, 15.5 | 7.0, 20.0 |
| Number of subjects by Month 12 | 37 | 43 |
| Number of new BCCs by Month 12- Mean (SD) | 3.08 (2.56) | 4.19 (5.31) |
| Median | 2.0 | 3.0 |
| Min, Max | 0, 8 | 0, 24 |
| Q1, Q3 | 1.0, 5.0 | 0.0, 6.0 |
| Total new BCCs | 114 | 180 |
| LS Mean for new BCCs per year (Std Err) | 2.83 (0.52) | 3.12 (0.54) |

TABLE 13-continued

| | Patidegib | Vehicle |
|---|---|---|
| 95% CI | (1.97, 4.07) | (2.22, 4.39) |
| Predicted new BCCs per year using observed covariates (95% CI) | 3.09 (2.18, 4.39) | 3.41 (2.49, 4.68) |
| Rate-ratio: Patidegib/Vehicle (Std Err) | 0.91 (0.22) | |
| 95% CI of Mean Ratio | (0.56, 1.47) | |
| p-value[1] | 0.6893 | |

As shown in Table 13, after 12 months of treatment with patidegib gel 2% the number of new BCC per subject is about 3.08, whereas for patients that were treated with vehicle is about 4.19 Therefore, administration of patidegib gel 2% prevents the formation of new BCCs in a subject with PTCH1 mutation in comparison to the administration of a vehicle.

Number of BCC surgeries by month 12 per subject in a subject with more than 6 BCC lesions at baseline, are shown in Table 14 below:

TABLE 14

| | Patidegib | Vehicle |
|---|---|---|
| Number of subjects from Baseline to month 12 | 22 | 32 |
| Number of BCCs surgeries - Mean (SD) | 0.6 (1.47) | 1.3 (2.31) |
| Median | 0.0 | 0.0 |
| Min, Max | 0, 5 | 0, 10 |
| Q1, Q3 | 0, 1 | 0, 2 |
| Total BCCs surgeries from Baseline to month 12 | 14 | 40 |

As shown in Table 14, after 12 months of treatment with patidegib gel 2% the number of BCC surgeries per subject is about 0.6, whereas for patients that were treated with the vehicle it is about 1.3. Therefore, administration of patidegib gel 2% reduces BCCs surgeries in a subject having at least 6 facial BCC lesions in comparison to the administration of a vehicle.

Example 3

A randomized, double-blind, stratified, vehicle-controlled study was done, measuring the efficacy and safety of Patidegib Topical Gel, 2%, applied topically twice daily to the face of adult participants with Gorlin syndrome. The Participants were required to apply the investigational product for 12 months. The primary endpoint is a comparison between the two treatment arms of the number of new BCCs that develop over the 12 month period.

Experimental: Patidegib Topical Gel, 2%,

Participants will be randomized to receive Patidegib Topical Gel, 2%. The Patidegib Topical Gel, 2% will be dispensed to participants at each study visit and applied topically twice daily to the face.

Placebo Comparator: Patidegib Topical Gel, Vehicle

Participants will be randomized to receive Vehicle. The Patidegib Topical Gel, Vehicle will be dispensed to participants at each study visit and applied topically twice daily to the face.

Criteria for Participant

Inclusion Criteria:

1. The participant must be age at least 18 years of age at the Screening Visit.
2. The participant must provide written informed consent prior to any study procedures.
3. The participant must meet diagnostic criteria for the basal cell nevus (Gorlin) syndrome including major criterion #3a plus 1 additional major criterion or plus 2 additional minor criteria listed below.

Major Criteria:

a. >2 histologically confirmed BCCs or 1 for participant under age 20.

b. Odontogenic keratocysts of the jaw confirmed histologically.

c. ≥3 palmar and/or plantar pits seen at the Screening Visit.

d. Bilamellar calcification of the falx cerebri present at less than 20 years of age.

e. Fused, bifid, or markedly splayed ribs.

f. First degree relative with Gorlin syndrome.

g. Patched protein 1 (PTCH1) mutation predicted to be of functional significance in normal tissue.

Minor Criteria:

h. Macrocephaly.

i. Congenital malformations including frontal bossing, cleft lip or palate, "coarse face", moderate to severe hypertelorism.

j. Skeletal abnormalities detectable clinically: Sprengel deformity, marked pectus deformity, or marked finger syndactyly.

k. Skeletal abnormalities detectable radiographically: bridging of the sella turcica; vertebral abnormalities such as hemivertebrae, fusion or elongation of the vertebral bodies; modeling defects of the hands and feet; flame shaped lucencies of the hands or feet.

l. Ovarian fibroma.

m. Medulloblastoma (Modification of criteria of V Kimonis et al Am J Med Genet 69: 299-308, 1997).

4. The participant must have 10 (with at least 3 on the face) clinically typical BCCs present within 24 months prior to Randomization (Baseline/Day 1). Additionally, the subject must have at least 2 BCCs with longest diameter <5 mm present on the face prior to Randomization (Baseline/Day 1).
5. The participant is willing to have blood collected to measure circulating drug levels.
6. The participant is willing to abstain from application of a non-study topical medication (prescription or over the counter) to facial skin for the duration of the trial except as prescribed by the Investigator. Moisturizers and emollients are allowed. Participant will be encouraged to use their preferred sunscreen with a sun protector factor (SPF) of at least 30 daily on all exposed skin sites.
7. If the participant is a woman of childbearing potential (WOCBP), she must be willing to use complete abstinence from sexual intercourse and/or she and her partner must be willing to use at least 2 highly-effective forms of birth control starting prior to Baseline, through the duration of the study, and for 12 months after last application of IP.
8. If the participant is a male with a female sex partner who is a WOCBP, the participant must be willing to use condoms, even after a vasectomy, starting prior to Baseline, through the duration of the study, and for at least 8 months after the last application of IP.
9. The participant is willing for all facial BCCs to be evaluated and treatment recommendations made only by the Investigator.
10. The participant is willing to forego treatment of facial BCCs with anything other than the study IP except when the Investigator believes that delay of treatment of a facial BCC potentially might compromise the health of the subject. During the trial the only allowed form of treatment is surgical. Non-facial BCCs may be removed at the discretion of the Investigator or Primary Skin Care Physician (PSCP).

Exclusion Criteria:

1. The subject has previously participated in a clinical trial evaluating patidegib topical gel.
2. The participant has used topical treatment to the face or systemic therapies that might interfere with the evaluation of the study IP. Among these are use of the following:

a. 5-fluorouracil, imiquimod, diclofenac, or Ingenol mebutate (except as topical treatment to discrete non-facial BCCs) systemically or topically to the skin within the 2 months prior to the Screening Visit.

b. Systemic chemotherapy within 1 year prior to the Screening Visit.

c. Known inhibitors of the Hedgehog signaling pathway (such as vismodegib, sonidegib, itraconazole) topically or systemically within 3 months prior to the Screening Visit.

d. Photodynamic therapy (PDT) except to localized non-facial, individual BCCs within 2 months prior to the Screening Visit.

3. The participant is known to have a hypersensitivity to any of the ingredients in the study medication formulation.
4. The participant is unable or unwilling to make a good faith effort to return to the study site for all study visits and tests.
5. The participant has uncontrolled systemic disease.
6. The participant has been treated for invasive cancer within the past 5 years excluding non-melanoma skin cancer, Stage I cervical cancer, ductal carcinoma in situ of the breast, or chronic lymphocytic leukemia (CLL) Stage 0.
7. The participant has current, recent (within five half-lives of the experimental drug or if half-life not known, within the past 6 months prior to the Screening Visit), or planned participation in an experimental drug study while enrolled in this study.
8. The participant is a WOCBP who is unwilling or unable to comply with pregnancy prevention measures.
9. The participant is pregnant or breastfeeding.
10. The participant has any condition or situation which, in the Investigator's opinion, may put the subject at significant risk, could confound the study results, or could interfere significantly with the subject's participation in the study. This may include a history of other skin conditions (such as severe facial eczema) or diseases, metabolic dysfunction, physical examination findings, or clinical laboratory findings giving reasonable suspicion of a disease or condition that contraindicates use of an investigational drug or that might affect interpretation of the results of the study or render the participant at high risk from treatment complications.

Results

Figure 13:
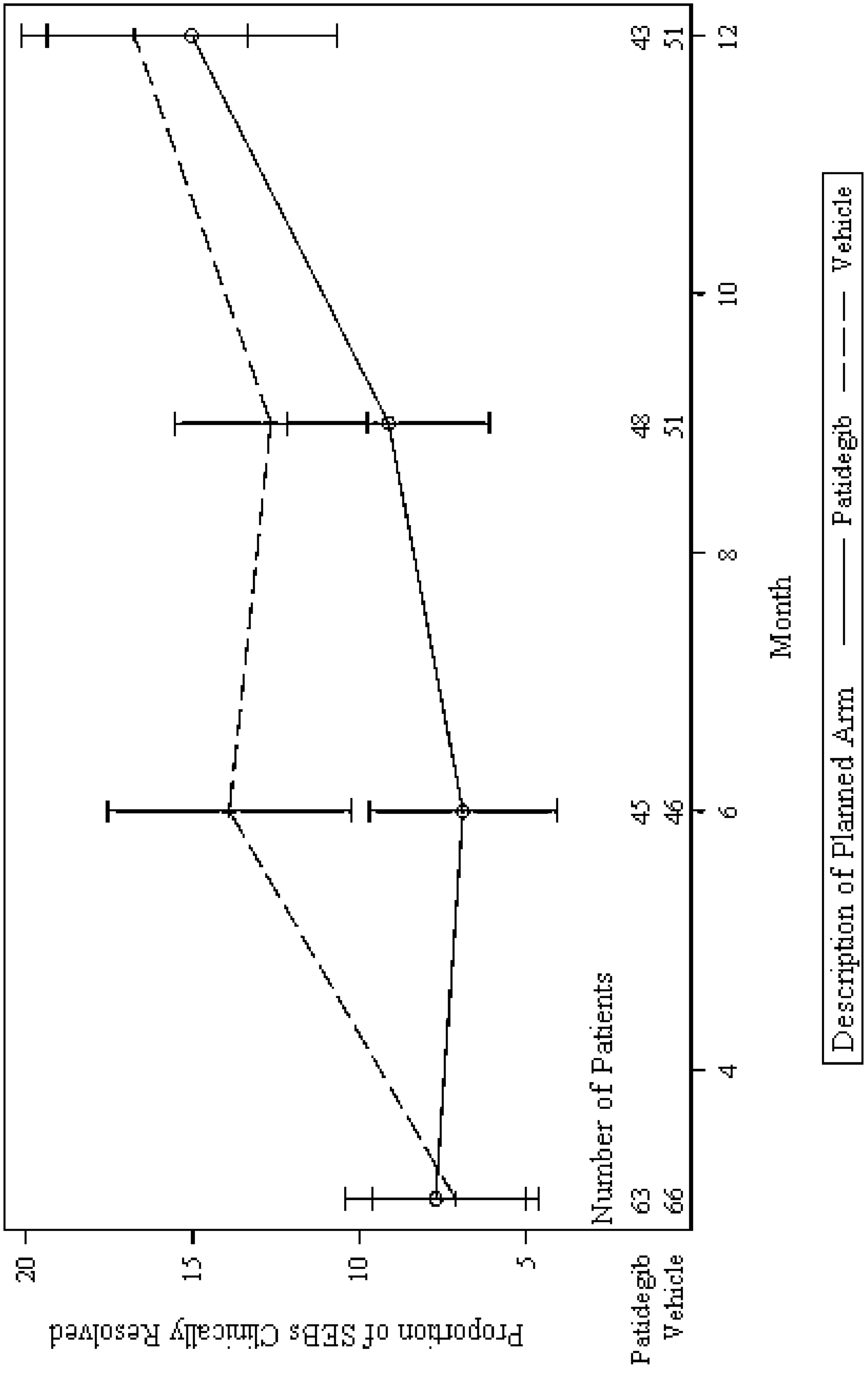
FIG. 13: Graphic illustration of proportion of SEBs resolved, intent to treat population (ITT), observed. Based on the study described in Example 3.

Proportion of SEBs clinically resolved, observed, in all types of the subjects of Example 3, the results are shown in FIG. 13 and table 15 as shown below:

TABLE 15

Analysis Variable: AVAL Analysis Value

| Description of Planned Arm | Analysis Visit (N) | N Obs* | N* | Mean | Std Error | Std Dev | Lower 95% CL for Mean | Upper 95% CL for Mean |
|---|---|---|---|---|---|---|---|---|
| Patidegib | 3 | 63 | 63 | 7.72 | 2.70 | 21.41 | 2.33 | 13.12 |
| | 6 | 45 | 45 | 6.91 | 2.81 | 18.84 | 1.25 | 12.57 |
| | 9 | 48 | 48 | 9.13 | 3.03 | 20.97 | 3.05 | 15.22 |
| | 12 | 43 | 43 | 15.03 | 4.33 | 28.39 | 6.30 | 23.77 |
| Vehicle | 3 | 66 | 66 | 7.14 | 2.47 | 20.05 | 2.21 | 12.06 |
| | 6 | 46 | 46 | 13.91 | 3.65 | 24.74 | 6.56 | 21.25 |
| | 9 | 51 | 51 | 12.66 | 2.87 | 20.52 | 6.89 | 18.43 |
| | 12 | 51 | 51 | 16.75 | 3.39 | 24.22 | 9.94 | 23.56 |

*N = number of patients

*Nobs = Number of patients with clinical data

As shown in Table 15 and FIG. 13, after 9 months of treatment with patidegib gel 2% the proportion of SEBs clinically resolved is about 9.13, whereas to patients that were treated with vehicle is about 12.66. After 12 months of treatment with patidegib gel 2% the number of qualifying SEBs is about 15.03, whereas to patients that were treated with vehicle is about 16.75. Therefore, administration of patidegib gel 2% does not affect the proportion of SEBs clinically resolved in all types of the subjects of the study of Example 3 in comparison to the administration of a vehicle.

Example 4

A post hoc analysis was performed on the results of the clinical trial of Example 3 to analyze the impact of Patidegib on patients without PTCH1 mutation.

Results

Figure 14:
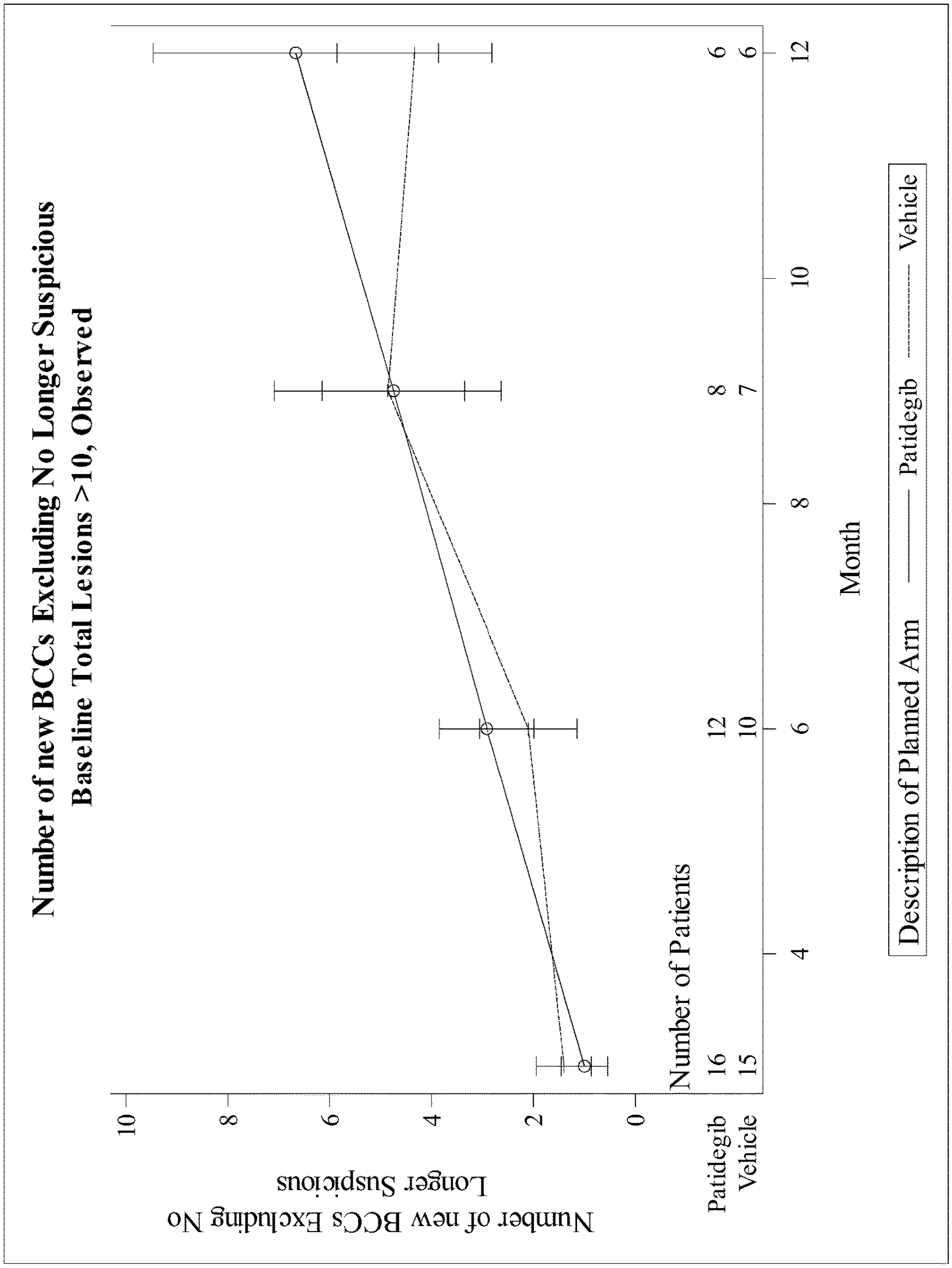
FIG. 14: Graphic illustration of number of new BCCs excluding no longer suspicious BCCs, observed, in a subject with Gorlin syndrome that does not have PTCH1 mutation and has at least 10 facial BCC lesions at baseline. Based on the study described in Example 4.

Number of new BCCs excluding no longer suspicious BCCs, observed, in a subject with Gorlin syndrome that does not have PTCH1 mutation and baseline total facial BCC lesions is at least 10, are shown in FIG. 14 and Table 16 as shown below:

TABLE 16

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 16 | 16 | 1.00 | 0.46 | 1.83 | 0.03 | 1.97 |
| | 6 | 12 | 12 | 2.92 | 0.93 | 3.23 | 0.86 | 4.97 |
| | 9 | 8 | 8 | 4.75 | 1.40 | 3.96 | 1.44 | 8.06 |
| | 12 | 6 | 6 | 6.67 | 2.80 | 6.86 | −0.53 | 13.87 |
| Vehicle | 3 | 15 | 15 | 1.40 | 0.54 | 2.10 | 0.24 | 2.56 |
| | 6 | 10 | 10 | 2.10 | 0.96 | 3.03 | −0.07 | 4.27 |
| | 9 | 7 | 7 | 4.86 | 2.23 | 5.90 | −0.60 | 10.31 |
| | 12 | 6 | 6 | 4.33 | 1.52 | 3.72 | 0.43 | 8.24 |

*N = number of patients
*Nobs = Number of patients with clinical data

As shown in Table 16 and FIG. 14, after 12 months of treatment with patidegib gel 2% the number of new BCCs per subject is about 6.67, whereas for patients that were treated with vehicle is about 4.33. Therefore, the administration of patidegib gel 2% does not prevent the formation of new BCCs in a subject that suffers from Gorlin syndrome and does not have PTCH1 mutation in comparison to the administration of a vehicle.

Figure 15:
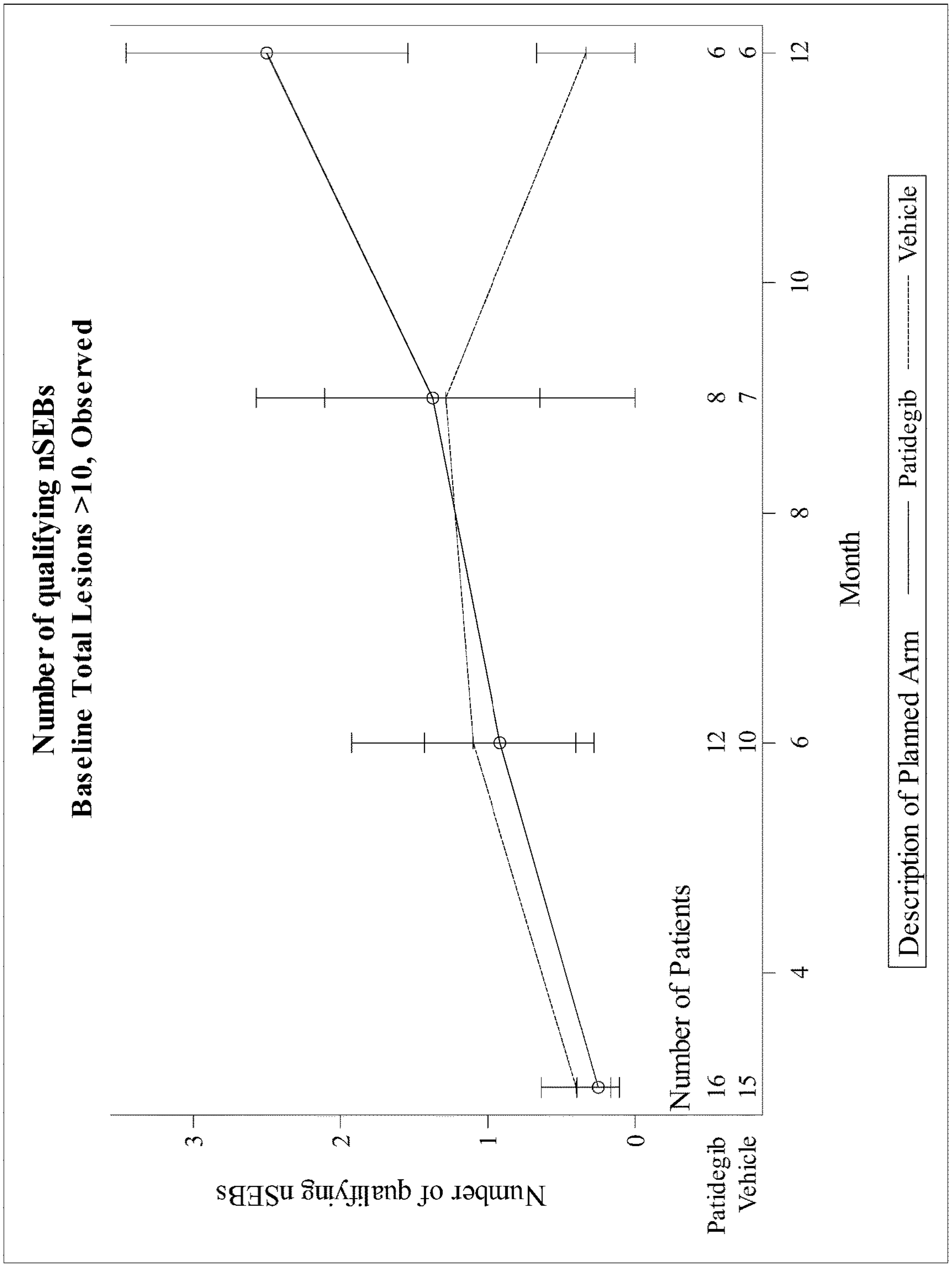
FIG. 15: Graphic illustration of number of qualifying nSEBs, observed, in a subject with Gorlin syndrome that does not have PTCH1 mutation and has at least 10 BCC lesions at baseline. Based on the study described in Example 4.

Number of qualifying nSEBs, observed, in a subject with Gorlin syndrome that does not have PTCH1 mutation and baseline total BCC lesions is at least 10, are shown in FIG. 15 and Table 17 as shown below:

TABLE 17

| Analysis Variable: AVAL Analysis Value | | | | | | | | |
|---|---|---|---|---|---|---|---|---|
| Description of Planned Arm | Analysis Visit (N) | N Obs* | N* | Mean | Std Error | Std Dev | Lower 95% CL for Mean | Upper 95% CL for Mean |
| Patidegib | 3 | 16 | 16 | 0.25 | 0.14 | 0.58 | −0.06 | 0.56 |
| | 6 | 12 | 12 | 0.92 | 0.51 | 1.78 | −0.22 | 2.05 |
| | 9 | 8 | 8 | 1.38 | 0.73 | 2.07 | −0.35 | 3.10 |
| | 12 | 6 | 6 | 2.50 | 0.96 | 2.35 | 0.04 | 4.96 |
| Vehicle | 3 | 15 | 15 | 0.40 | 0.24 | 0.91 | −0.10 | 0.90 |
| | 6 | 10 | 10 | 1.10 | 0.82 | 2.60 | −0.76 | 2.96 |
| | 9 | 7 | 7 | 1.29 | 1.29 | 3.40 | −1.86 | 4.43 |
| | 12 | 6 | 6 | 0.33 | 0.33 | 0.82 | −0.52 | 1.19 |

*N = number of patients
*Nobs = Number of patients with clinical data

As shown in Table 17 and FIG. 15, after 9 months of treatment with patidegib gel 2% the number of qualifying nSEBs is about 1.38, whereas to patients that were treated with vehicle is about 1.29. After 12 months of treatment with patidegib gel 2% the number of qualifying nSEBs is about 2.5, whereas to patients that were treated with vehicle is about 0.33. Therefore, administration of patidegib gel 2% does not reduce the number of qualifying nSEBs in Gorlin subject without PTCH1 mutation and baseline total facial BCC lesions of at least 10.

As shown in Example 2, the administration of Patidegib to a subject suffering from Gorlin syndrome and have a genetic mutation PTCH1 is effective in treating or preventing BCC lesions. In contrast, as shown in Examples 3 and 4, the administration of Patidegib produced no effect in subjects with Gorlin syndrome who lacked the PTCH1 mutation. This is unexpected, particularly when compared to known oral drugs Vismodegib and Sonidegib, also Hedgehog (Hh) pathway inhibitors, which are known to effect patients with Gorlin Syndrome, both with and without PTCH1 mutation.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treatment and/or prevention of basal cell carcinoma (BCC) lesions in a patient suffering from Gorlin syndrome, the method comprising screening the patient for genetic mutation PTCH1; and topically administering a pharmaceutical composition comprising patidegib or a pharmaceutically acceptable salt thereof, and a pharmaceutically acceptable carrier, to the patient if the screening confirms that the patient has the genetic mutation PTCH1, and wherein the patidegib is in an amount of about 2% w/w to about 4% w/w.

2. The method of claim 1, wherein the subject has at least 6 BCC lesions.

3. The method of claim 1, wherein the patidegib is in an amount of 2%, 3% or 4% w/w.

4. The method of claim 1, wherein the patidegib is formulated as a gel or a cream formulation.

5. The method of claim 1, wherein the method of treatment of the basal cell carcinoma (BCC) lesions results in a reduction of BCC lesion size or resolved BCC lesions over time.

6. The method of claim 1, wherein the method resolves and/or reduces the size of surgically eligible BCC lesions.

7. The method of claim 1, wherein the method of prevention of the basal cell carcinoma (BCC) lesions refers to preventing formation of new BCC lesions, or new surgically eligible BCC lesions.

8. The method of claim 1, wherein the pharmaceutical composition is topically administered once daily, twice daily, trice daily, every other day, three times a week, or once a week.

9. The method of claim 8, wherein the pharmaceutical composition is topically administered for a period of about 3 months, about 6 months, about 9 months, about 12 months, more than about 12 months, or for a lifetime.

10. The method of claim 1, wherein the subject does not develop drug resistance.

11. The method of claim 1, wherein following a discontinuation period of administration during the treatment, the drug efficacy is not affected.

* * * * *